US012678383B2

(12) United States Patent
Hoelscher et al.

(10) Patent No.: US 12,678,383 B2
(45) Date of Patent: Jul. 14, 2026

(54) FRAGRANCE COMPOSITIONS CONTAINING 1,3-PROPANEDIOL

(71) Applicant: SYMRISE AG, Holzminden (DE)

(72) Inventors: Bernd Hoelscher, Halle (DE); Julia Amos, Eschershausen (DE)

(73) Assignee: SYMRISE AG, Holzminden (DE)

( * ) Notice: Subject to any disclaimer, the term of this patent is extended or adjusted under 35 U.S.C. 154(b) by 1057 days.

(21) Appl. No.: 17/627,326

(22) PCT Filed: Jul. 16, 2020

(86) PCT No.: PCT/EP2020/070208
§ 371 (c)(1),
(2) Date: Jan. 14, 2022

(87) PCT Pub. No.: WO2021/009315
PCT Pub. Date: Jan. 21, 2021

(65) Prior Publication Data

US 2022/0273537 A1 Sep. 1, 2022

(30) Foreign Application Priority Data

Jul. 16, 2019 (WO) ................. PCT/EP2019/069171

(51) Int. Cl.
*A61K 8/34* (2006.01)
*A61Q 13/00* (2006.01)

(52) U.S. Cl.
CPC .............. *A61K 8/345* (2013.01); *A61Q 13/00* (2013.01)

(58) Field of Classification Search
CPC .................................. A61Q 13/00; C11B 9/00
See application file for complete search history.

(56) References Cited

U.S. PATENT DOCUMENTS

| | | | |
|---|---|---|---|
| 2003/0068295 A1 | 4/2003 | Rohde et al. | |
| 2003/0147937 A1 | 8/2003 | Schwarz | |
| 2006/0089413 A1 | 4/2006 | Schmaus et al. | |
| 2007/0241306 A1 | 10/2007 | Wehner et al. | |
| 2008/0050319 A1 | 2/2008 | Koch et al. | |
| 2008/0070825 A1 | 3/2008 | Bertram et al. | |
| 2009/0028804 A1 | 1/2009 | Krutmann et al. | |
| 2013/0236620 A1 | 9/2013 | Herrera-Gomez et al. | |
| 2016/0296459 A1* | 10/2016 | Sun | C11D 3/43 |
| 2018/0116267 A1* | 5/2018 | Dierbach | A23L 9/10 |
| 2020/0010402 A1 | 1/2020 | Chandrasekaran et al. | |

FOREIGN PATENT DOCUMENTS

| | | | | |
|---|---|---|---|---|
| EP | 2822401 B1 | 1/2015 | | |
| EP | 2926673 A1 | 10/2015 | | |
| EP | 3440942 A1 | 2/2019 | | |
| WO | WO-01/43784 A2 | 6/2001 | | |
| WO | WO-01/76572 A2 | 10/2001 | | |
| WO | WO-02/15686 A1 | 2/2002 | | |
| WO | WO-2005/107692 A1 | 11/2005 | | |
| WO | WO-2005/123101 A1 | 12/2005 | | |
| WO | WO-2006/015954 A1 | 2/2006 | | |
| WO | WO-2006/045760 A1 | 5/2006 | | |
| WO | WO-2006/053912 A1 | 5/2006 | | |
| WO | WO-2007/042472 A1 | 4/2007 | | |
| WO | WO-2007/060256 A2 | 5/2007 | | |
| WO | WO-2007/110415 A2 | 10/2007 | | |
| WO | WO-2007/128723 A1 | 11/2007 | | |
| WO | WO-2008/046676 A1 | 4/2008 | | |
| WO | WO-2008/046791 A1 | 4/2008 | | |
| WO | WO-2008/046795 A1 | 4/2008 | | |
| WO | WO-2016/164205 A1 | 10/2016 | | |
| WO | WO-2017097434 A1 * | 6/2017 | | A61K 8/4973 |
| WO | WO-2018114073 A1 * | 6/2018 | | A23L 27/2028 |

OTHER PUBLICATIONS

Anonymous, 1-Hexanol, PubChem, https://pubchem.ncbi.nlm.nih.gov/compound/8103, accessed Feb. 6, 2025 (Year: 2025).*
Anonymous, 1-Octanol, PubChem, https://pubchem.ncbi.nlm.nih.gov/compound/957, accessed Feb. 6, 2025 (Year: 2025).*
Anonymous, 1-Heptanol, PubChem, https://pubchem.ncbi.nlm.nih.gov/compound/8129, accessed Feb. 6, 2025 (Year: 2025).*
Anonymous, Phenylethyl Alcohol, PubChem, https://pubchem.ncbi.nlm.nih.gov/compound/6054, accessed Feb. 6, 2025 (Year: 2025).*
Anonymous, Linalool, PubChem, https://pubchem.ncbi.nlm.nih.gov/compound/6549, accessed Feb. 6, 2025 (Year: 2025).*
Anonymous, Citronellol, PubChem, https://pubchem.ncbi.nlm.nih.gov/compound/8842, accessed Feb. 6, 2025 (Year: 2025).*
Anonymous, Geraniol, PubChem, https://pubchem.ncbi.nlm.nih.gov/compound/637566, accessed Feb. 6, 2025 (Year: 2025).*
Anonymous, Nerol, PubChem, https://pubchem.ncbi.nlm.nih.gov/compound/643820, accessed Feb. 6, 2025 (Year: 2025).*
Anonymous, Eugenol, PubChem, https://pubchem.ncbi.nlm.nih.gov/compound/3314, accessed Feb. 6, 2025 (Year: 2025).*
Arce et al., "Propanediols for separation of citrus oil: liquid-liquid equilibria of limonene + linalool + (1,2-propanedoil or 1,3-propanedoil)," Fluid Phase Equilibria 211:129-149 (2003).

(Continued)

*Primary Examiner* — Bethany P Barham
*Assistant Examiner* — Paul Hoerner
(74) *Attorney, Agent, or Firm* — MARSHALL, GERSTEIN & BORUN LLP

(57) ABSTRACT

Provided are non-aqueous perfume mixtures comprising 1,3-propanediol and one or more perfume(s), in particular from the group of odorant alcohols with green notes and/or the group of odorant alcohols with floral notes, a process for the preparation of the perfume mixtures, a process for modifying the sensory properties of a perfume, the use of 1,3-propanediol for modifying sensory properties of a perfume in a perfume mixture and for the preparation of a perfume mixture, the use of the perfume mixtures for the preparation of perfumed products, perfumed products containing the perfume mixtures in a sensory effective amount and a process for the preparation of the perfume mixtures.

9 Claims, No Drawings

(56) References Cited

OTHER PUBLICATIONS

Arctander, "Perfume and Flavor Chemicals," front matter and table of contents, self-publication (1969).
International Search Report and Written Opinion from International Application No. PCT/EP2020/070208 dated Oct. 13, 2020.
Surburg et al., "Common Fragrance and Flavor Materials," 6th Edition, front matter and table of contents, Wiley-VCH, Weinheim (2016).
International Search Report and Written Opinion from priority application, International Application No. PCT/EP2019/069171 dated Apr. 15, 2020.

* cited by examiner

FRAGRANCE COMPOSITIONS CONTAINING 1,3-PROPANEDIOL

CROSS-REFERENCE TO RELATED APPLICATIONS

This is a U.S. National Phase of International Application No. PCT/EP2020/070208, filed Jul. 16, 2020, which claims priority to International Application No. PCT/EP2019/069171, filed Jul. 16, 2019, the contents of which are incorporated herein by reference.

FIELD OF THE INVENTION

The invention is in the field of fragrances and relates to non-aqueous perfume mixtures having modified sensory properties, a process for preparing the perfume mixtures, a process for modifying the sensory properties of a fragrance, the use of 1,3-propanediol for modifying sensory properties of a perfume in a perfume mixture and for the preparation of a perfume mixture, the use of the perfume mixtures for the preparation of perfumed products, perfumed products containing the perfume mixtures in a sensory effective amount, and a process for the preparation of the perfume mixtures.

In principle, there is a constant need on the part of the perfume industry and in the manufacture of perfumed products to enhance (highlight/emphasize) pleasant olfactory aspects of fragrances and to mask or reduce unpleasant olfactory aspects. Especially floral fragrances, i.e. fragrances with a floral note, play an important role in perfumery. Thereby, it is desirable to particularly emphasize their natural freshness and/or radiance on the one hand and to suppress their greasy, metallic and/or technical notes on the other hand.

The reduction of unpleasant odors is a problem that is difficult to solve in terms of perfumery composition. Above all, the specific character of a particular unpleasant odor severely restricts the possible applications. Often, a reduction of unpleasant odors can at best be achieved by combinations with a specially developed perfume oil which itself has its own, very specific scent type. In this case, the unpleasant odor impressions are often merely masked with the help of fragrant odors of a (different) substance.

Numerous suggestions for eliminating unpleasant odors can be found in the literature, as exemplified below.

WO 01/43784 A2 and US 2003 068295 A1 describe the use of certain esters, in particular isomenthyl esters such as isomenthyl acetate, as odor-neutralizing substances for reducing unpleasant odors of various kinds.

WO 2016/164205 A1 discloses aqueous multilamellar composition for delivering a hydrophobic substance comprising 50 to 80% by weight of phenylethyl alcohol and/or phenylpropyl alcohol and optionally 10 to 20% by weight of 1,3-propanediol. 1,3-propanediol is used therein as a solubilizer.

EP 2 822 401 and EP 3 440 942 A1 relate to foods and beverages comprising 1,3-propanediol for flavor modification. The amount of 1,3-propanediol used is 0.01 to 5 wt. % and 0.1 to 2 wt-%, respectively.

US 2007 0241306 A1 discloses numerous biodegradable compositions comprising 1,3-propanediol.

EP 2 926 673 A1 relates to substance mixtures comprising terpene, 1,3-propanediol and active ingredients such as, for example, rebaudiosides, steviosides. 1,3-propanediol is used in these substance mixtures in an amount of 20 to 80% by weight.

Previous (smelling) substances or (smelling) substance mixtures, which aim at an odor enhancement of products, often show an unsatisfactory odor reduction of unpleasant odors. In the methods known in the prior art for reducing unpleasant odors, there is often the disadvantage that the (odoriferous) substances or (odoriferous) substance mixtures used have to be used in considerable quantities, which can lead to cost and application problems.

Substances or substances which are capable of intensifying the intensity of pleasant odors and/or masking, reducing or even completely eliminating unpleasant odors without themselves being of appreciable odorous perfumery intensity or without themselves being of appreciable odorous perfumery intensity in the concentration to be used for the purposes of odor intensification and/or odor reduction are therefore of considerable advantage.

In the case of olfactory alcohols, which play an important role in perfumery, this applies in particular to their natural freshness and floral appeal on the one hand and their musty, artificial and metallic notes on the other.

The use of the above substances or materials should also be such that they can be used for scenting or perfuming any fragrance.

Advantageously, these substances or materials should originate from natural or sustainably produced raw materials and, in addition to the properties listed above, should have other positive properties such as an antibacterial effect.

There is an even greater need for substances or materials that do not have any adverse health effects.

In the perfumery sector, for example in the preparation or production of perfume mixtures, 1,2-propanediol (propylene glycol) or dipropylene glycol were mainly used as common solvents in the past.

The compound 1,3-propanediol is known from the prior art. In the perfumery field, 1,3-propanediol has not found any significant application so far. In particular, the mention of specific proportions in the preparation of perfume mixtures is not known, and a fortiori no odorous effect is known when combined with any perfume substance(s).

It was therefore a primary object of the present invention to provide alternative or improved substances or materials, for example additives or solvents, for modifying sensory properties of fragrances in non-aqueous perfume mixtures. These should also be accessible from natural sources.

Such substances should preferably meet one, more or preferably all of the following requirements:

- easy accessibility, i.e. production from natural and sustainably produced raw materials,
- high efficacy in low concentrations, preferably with no or hardly perceptible intrinsic odor in low concentrations,
- extensive or complete colourlessness,
- high stability in various mixtures or preparations, whereby in particular no discoloration and/or separation and/or turbidity should occur,
- inert behavior,
- no toxic and/or allergenic effect towards humans.

Furthermore, the present invention was intended to provide new, advantageous non-aqueous perfume mixtures, in particular perfume oils containing such substances, and a process for preparing such perfume mixtures.

Such perfume mixtures should preferably be suitable for fragrancing or perfuming certain products.

Accordingly, perfumed products containing such a non-aqueous perfuming mixture should also be indicated, as well as a process for the preparation of such perfumed products.

Further tasks underlying the present invention will be apparent from the following explanations and the appended patent claims.

SUMMARY OF THE INVENTION

A first object of the invention relates to a non-aqueous perfume mixture, preferably a perfume oil, comprising or consisting of (i) >10% by weight of 1,3-propanediol; and
(ii) one or more odorant(s) from the group of odorant alcohols, preferably from the group of odorant alcohols with green odor notes and/or the group of odorant alcohols with floral odor notes.

In a second aspect, the present invention relates to a method of preparing a non-aqueous perfume mixture comprising the steps of:

providing 1,3-propanediol;
providing an odorant alcohol or several odorant alcohols from the group of odorant alcohols, preferably from the group of odorant alcohols with green notes and/or the group of odorant alcohols with floral notes.
contacting and mixing an effective amount of >10% by weight of 1,3-propanediol with the one or more odorant alcohols to obtain the non-aqueous perfuming mixture.

The third object of the present invention is to provide a method for modifying the sensory properties of one or more odorant alcohols, comprising the steps of: Mixing an odorant alcohol or alcohols with an effective amount of >10% by weight of 1,3-propanediol in order to emphasise or accentuate a pleasant odor note or all the pleasant odor notes of an odorant alcohol or of several odorant alcohols,
preferably highlighting or accentuating the pleasant odor note(s) more radiance, natural freshness or floral odor note(s) of an odorant alcohol or of several odorant alcohols;

and/or mask or reduce an unpleasant odor note or all unpleasant odor notes of an odorant alcohol or several odorant alcohols,
preferably masking or reducing the unpleasant odor note (s) of musty, greasy, technical or metallic odor note(s) of an odorant alcohol or of several odorant alcohols.

In a fourth aspect, the present invention relates to the use of 1,3-propanediol in an effective amount for modifying the sensory properties of one or more odorant alcohols, in particular to accentuate or enhance a pleasant odor note or all pleasant odor notes of one or more odorant alcohols; or of more than one odorant alcohol;

and/or for masking or reducing an unpleasant odor note or all unpleasant odor notes of one or more odorant alcohols of more than one odorant alcohol.

The fifth object of the present invention is the use of 1,3-propanediol for preparing a non-aqueous perfume composition comprising or consisting of (i) >10% by weight of 1,3-propanediol; and
(ii) one or more odorant(s) selected from the group consisting of odorant alcohols, preferably from the group consisting of odorant alcohols with green odor notes and/or the group consisting of odorant alcohols with floral odor notes.

In a sixth aspect, the present invention relates to the use of the non-aqueous perfume mixture or perfume mixture according to the invention in a sensory effective amount for modifying an odor note in a perfumed product or for preparing a perfumed product.

In another aspect, the present invention relates to a perfumed product comprising a sensory effective amount of the non-aqueous odor mixture or perfume mixture according to the invention.

Finally, in another aspect, the present invention relates to a method of making a perfumed product comprising the steps of:

(a1) providing the perfume mixture according to the invention,
(b1) providing a further constituent or constituents of the perfumed product to be produced; and
(c1) contacting or mixing a sensory effective amount of the perfume mixture provided in step (a1) with the further ingredient(s) provided in step (b1) to obtain the perfumed product;

the amount of 1,3-propanediol (i) being >10% by weight, based on the total weight of the perfuming composition, in order to accentuate or enhance a pleasant odor note or all pleasant odor notes of the odorant alcohol(s) (ii) of the odorant mixture,
preferably to bring out or accentuate the radiance, natural freshness or floral olfactory notes of the one or more odorant alcohols (ii) of the perfuming mixture; and/or
an unpleasant odor note or all of the unpleasant odor notes of the one or more odorant alcohols (i) of the perfume mixture olfactory alcohols (ii) of the odorant mixture to mask or reduce, preferably mask or reduce the musty, fatty, technical or metallic odor notes of the one or more odorant alcohols; and olfactory alcohols;

or (a2) providing one or more odorant alcohols (ii) of the perfume mixture according to the invention,
(b2) providing a further component or components of the perfumed product to be manufactured,
(c2) mixing a sensory effective amount of the one or more odorant alcohols provided in step (a2) (ii) with the further ingredient(s) provided in step (b2) to obtain a mixture, and
(d2) contacting the mixture obtained in step (c2) with 1,3-propanediol, the amount of 1,3-propanediol being >10% by weight, based on the total weight of the perfuming composition, in order to emphasize or accentuate a pleasant odor note or all the pleasant odor notes of the one odorant alcohol or of the several odorant alcohols (ii),
preferably to bring out or accentuate the radiance, natural freshness or floral olfactory notes of the one or more odoriferous alcohols (ii); and/or
an unpleasant odor note or all of the unpleasant odor notes of the one or more odorant alcohols (ii) mask or reduce the odor, preferably masking or reducing the musty, fatty, technical or metallic odors of the one or more odorant alcohols (ii).

These and other aspects, features and advantages of the present invention will be apparent to those skilled in the art from a study of the following detailed description and claims. In this regard, any feature from one aspect of the invention may be used or substituted in another aspect of the invention. Furthermore, it is understood that the examples contained in the present application describe and illustrate the invention but do not limit it and, in particular, that the present invention is not limited to these examples.

All percentages are by weight unless otherwise stated. Numerical examples given in the form "from x to y" include the values given. When multiple preferred numeric ranges are given in this format, it is understood that all ranges created by combining the various endpoints are also included.

DETAILED DESCRIPTION OF THE INVENTION

In a first aspect, the present invention relates to a non-aqueous perfume mixture, preferably a perfume oil, comprising or consisting of (i) >10% by weight of 1,3-propanediol; and (ii) one or more odorant(s) from the group of odorant alcohols, in particular from the group of odorant alcohols with green odor notes and/or the group of odorant alcohols with floral odor notes.

The perfume mixture according to the present invention is a non-aqueous perfume mixture. The term "non-aqueous" perfume mixture in the context of the present invention is understood to mean a perfume mixture characterized by having a water content of less than about 1% by weight or being completely free of water. In the following description, the term "perfume mixture" is always understood to mean a non-aqueous perfume mixture, even if this is not explicitly stated.

The first ingredient (i) of the perfume mixture according to the invention is 1,3-propanediol. 1,3-propanediol consists of the basic skeleton of propane, at each of whose terminal positions there is a hydroxyl group. 1,3-Propanediol belongs to the group of divalent alcohols, the diols. It is a colourless, hygroscopic liquid with only a faint odor or none at all.

1,3-Propanediol can be produced biotechnologically either by chemical synthesis or by microorganisms from corn or from glycerol, which is a by-product of the transesterification of vegetable oils during the production of biodiesel from rapeseed oil. Consequently, it is a sustainably produced product that is easily accessible.

In perfumery, 1,3-propanediol has not been used to any significant extent, in particular as a solvent in the preparation and manufacture of perfume mixtures.

In the perfumery sector, for example in the preparation or production of perfume mixtures, 1,2-propanediol or dipropylene glycol were predominantly used as common solvents in the past.

1,2-Propanediol is a clear colorless, almost odorless and strongly hygroscopic liquid. Due to its solvent and emulsifying properties, 1,2-propanediol is used, among other things, as a carrier or carrier solvent for dyes, flavors, emulsifiers, etc., or is used in cosmetic products such as skin creams, toothpaste, mouthwashes and deodorants primarily as a solvent or humectant.

Industrially, 1,2-propanediol is produced synthetically by hydrolysis of propylene oxide. Depending on the manufacturer, either a high-temperature process without catalysis at 200 to 220° C. or a catalytic process at 150 to 180° C. in the presence of an ion-exchange resin or no amounts of sulfuric acid or alkalis are used for this purpose. The disadvantage of 1,2-propanediol as a solvent is that it forms acetals with fragrances having aldehyde functionality. Acetal formation results in a change and thus a deterioration of the odor profile.

Dipropylene glycol (DPG) is a by-product of the manufacture of 1,2-propanediol. Dipropylene glycol is a colorless, hygroscopic, viscous, odorless and low-volatility liquid. Dipropylene glycol, as an isomeric mixture of three structural isomers, is used either as a solvent for odor-sensitive applications such as flavors or as a humectant for a variety of cosmetic applications.

Both solvents are not made from natural raw materials.

Compared to 1,2-propanediol or dipropylene glycol (DPG), 1,3-propanediol is characterized by the fact that it can be obtained from natural or sustainably produced raw materials.

1,3-Propanediol has additional positive secondary properties over and above its primary sensory properties. These secondary properties include: high stability under certain application conditions, for example in alkaline media, e.g. washing powder, fabric softener, soaps, shampoos, etc. Furthermore, 1,3-propanediol is shown to be less reactive than 1,2-propanediol and thus inert to odorants, whereby in combination with one or more odorant(s) the odor profile is not adversely altered, for example by the degradation of odorants or by the formation of by-products. Furthermore, 1,3-propanediol exhibits an antibacterial effect.

It was also surprising that 1,3-propanediol of the perfume mixture according to the invention can be permanently and stably incorporated into a variety of different formulations.

The second ingredient (ii) of the perfume mixture according to the invention is a single perfume or a mixture of two, three, four, five, six, seven, eight, nine or more different odorants selected from the group consisting of odorant alcohols.

The odorant alcohols used in accordance with the invention are compounds having C6 to C11 carbon atoms and exhibiting OH group functionality.

Such odorant alcohols represent a very important group of perfumes in perfumery and are known to the skilled person in principle. A description of the olfactory properties of the odorant alcohols can be found, among others, in the reference book "S. Arctander: Perfume and Flavor Materials, Volumes I and II, Montclair, N.J., 1969, self-published". Examples of odorant alcohols are disclosed in "H. Surburg, J. Panten: Common Fragrance and Flavor Materials, 6th Edition, Wiley-VCH, Weinheim, 2016". The related disclosure in both literature sources is incorporated by specific reference in its entirety in the present application.

The olfactory alcohols are characterized either by a floral, soft or sweet scent and often form the basis for floral fragrance compositions or are characterized by a fresh, green or metallic scent. The terms "floral", "fresh", "green", "metallic" are standard terms from the classification system of basic odors or odor qualities and the scent or fragrance area as defined in the standard literature cited above.

Surprisingly, the presence of 1,3-propanediol in a perfume mixture according to the invention has the effect of modifying, i.e. highlighting or emphasizing and/or masking or diminishing, certain olfactory aspects of the one or more odorant alcohols.

Surprisingly, 1,3-propanediol in a perfume mixture has the effect that in particular the positive, i.e. pleasant odor notes, such as radiance, natural freshness or the flowery odor notes of an odorant alcohol or all odorant alcohols are emphasized or highlighted, i.e. intensified, and/or the negative, i.e. unpleasant odor notes, such as musty, fatty, technical or metallic odor notes of an odorant alcohol or all odorant alcohols are masked and/or the negative, i.e. unpleasant odor notes such as musty, fatty, technical or metallic odor notes of an odorant alcohol or all odorant alcohols are masked or reduced.

With regard to the terms 'highlighting' or 'emphasising', in the context of the present application, it is understood to mean an enhancement of the intensity of a positive, pleasant odor, in particular odors or odor notes of the type of more radiance, natural freshness, floral odor notes and/or similar odors, as opposed to being overlaid/covered by another dominant odor note.

In accordance with a preferred aspect of the present invention, 1,3-propanediol is particularly useful for masking or reducing, especially reducing, one or more unpleasant odor notes of one or more odorant alcohols.

With respect to the term "masking", it should be noted in the context of the present invention that this refers to a particular form of odor modification, namely the neutralization of, for example, an unpleasant odor as opposed to overlaying/covering by another dominant odor.

With regard to the term 'reducing', it should be noted that it refers to a particular form of odor change, namely the attenuation of the intensity of, for example, an unpleasant odor as opposed to it being overlaid/covered by another dominant odor note. In the context of the present application, a reduction of unpleasant odor notes is understood to mean a partial or a complete reduction, i.e. elimination, of unpleasant odors by a particular substance or mixture of substances, in particular odors or odor notes of the musty, greasy, technical, metallic and/or similar type.

The 1,3-propanediol to be used according to the invention is advantageously easily accessible or producible. can be produced, is highly effective even in low concentrations, in particular in concentrations at which 1,3-propanediol has no odor or at least only a barely perceptible odor of its own, is largely or completely colourless, is inert to odorous substances, so that in combination with one or more odorous substance(s) the odor profile is not adversely changed, has a high stability in different mixtures or preparations and has no toxic and/or allergenic effect on humans.

In addition, 1,3-propanediol has an antibacterial effect, a property that gives the resulting products microbial stability and thus shelf life.

1,3-Propanediol also has the advantage that in its use, in particular a use according to the invention, it can be combined with different fragrances and usual components of a perfume mixture to perfume products with any desired fragrance. Consequently, a wide range of fragrance types can be offered to consumers by the present invention.

The unpleasant-smelling substances mentioned herein may have other sensory qualities, including odor qualities, which are generally not unpleasant. Thus, as used herein, unpleasant smelling substances are generally understood to be those that elicit one or more unpleasant olfactory sensations or notes, whether as a primary odor or as a secondary/subordinate odor note. In particular, the unpleasant smelling substances described herein may also be those odoriferous substances which are primarily perceived as pleasant smelling substances, but which also have an unpleasant metallic, greasy and/or technical odor note which it is preferable to reduce according to the invention.

The same applies analogously to the pleasant-smelling substances described herein. In the context of the present text, pleasant-smelling substances are generally understood to be substances that evoke one or more pleasant odor impressions or odor notes, whether as a primary odor or as a secondary/subordinate odor note.

As a result, in the context of the present invention, for example, both an unpleasant odor note of a particular (unpleasant-smelling) substance can be masked or reduced, and a pleasant odor note of the same (also pleasant-smelling) substance can be enhanced.

The one, more or all of the odorant alcohol(s) whose odor properties are improved by the use of 1,3-propanediol according to the invention is preferably an odorant alcohol with a green odor note or an odorant alcohol with a floral odor note.

Generally preferred is such a perfume mixture according to the invention, in which the one, the several or all of the unpleasant and/or pleasant-smelling odorant alcohol(s) with a green odor note is/are selected from the group consisting of odorant alcohols having a molecular weight in the range from 100 g/mol to 190 g/mol, preferably in the range from 100 g/mol to 158 g/mol.

In a preferred embodiment, the invention relates to a perfume mixture, preferably a perfume oil, wherein the one or more odorant alcohols having a green odor note, is/are selected from the group consisting of C6 alcohol, C7 alcohol, (Z)-3-hexenol (cis-3-hexenol), (E)-2-hexenol (trans-2-hexenol), (E/Z)-3-hexenol and (Z)-4-hexenol (cis-4-hexenol), as listed in Table 1 below:

TABLE 1

| No. | Fragrance-alcohol Group | Name Molecular weight (MG) | Structure |
|---|---|---|---|
| 1 | Green | Alcohol C6 MG: 102.162 g/mol | 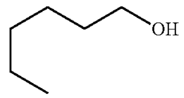 |
| 2 | Green | Alcohol C7 MG: 116.88 g/mol | 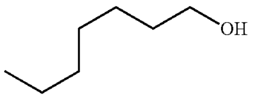 |
| 3 | Green | (Z)-hexenol MG: 100.16 g/mol | 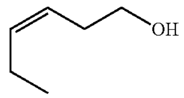 |
| 4 | Green | (E)-2-hexenol MG: 100.16 g/mol | 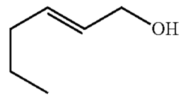 |
| 5 | Green | (E/Z)-3-hexenol MG: 100.16 | 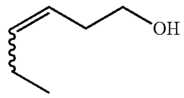 |
| 6 | Green | (Z)-4-hexenol MG 100.16 g/mol | |

Particularly preferred is a perfume mixture, preferably a perfume oil, in which the one or more odorant alcohols having a green odor note is/are selected from the group consisting of C6 alcohol, C7 alcohol, (Z)-3-hexenol (cis-3-hexenol) and (Z)-4-hexenol (cis-4-hexenol).

Alternatively preferred is such a perfume mixture according to the invention, preferably a perfume oil, in which the one, the several or all of the unpleasant and/or pleasant-smelling odorant alcohol(s) having a floral odor note is/are selected from the group consisting of odorant alcohols having a molecular weight in the range from 120 g/mol to 200 g/mol, preferably in the range from 122 to 168 g/mol.

In a preferred embodiment, the invention relates to a perfume mixture in which the one or more odorant alcohols having a floral odor note is/are selected from the group consisting of phenylethyl alcohol, linalool, citronellol, geraniol, nerol, ethyllinalool, tetrahydrolinalool, dihydromyrcenol, C8 alcohol, C9 alcohol, C10 alcohol, alpha-terpineol and tetrahydromyrcenol as listed in Table 2 below:

TABLE 2

| No. | Fragrance-alcohol Group | Name Molecular weight (MG) | Structure |
|---|---|---|---|
| 1 | Flowery | Phenylethyl alcohol MG: 122.16 g/mol | 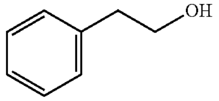 |
| 2 | Flowery | Linalool MG: 154.25 g/mol | 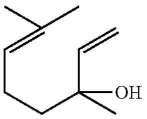 |
| 3 | Flowery | Citronellol MG: 156.27 g/mol | 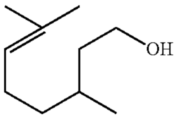 |
| 4 | Flowery | Geraniol MG: 154.25 g/mol | 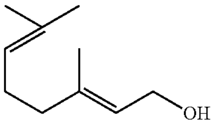 |
| 5 | Flowery | Nerol MG: 154.25 g/mol | 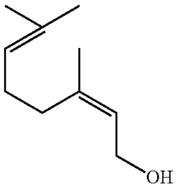 |
| 6 | Flowery | Ethyllinalool MG: 168.28 g/mol | 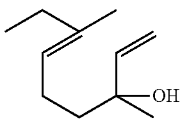 |
| 7 | Flowery | Tetrahydrolinalool MG: 158.285 g/mol | 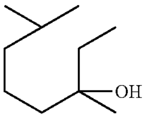 |
| 8 | Flowery | Dihydromyrcenol MG: 156.27 g/mol | 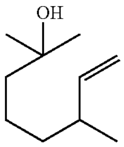 |
| 9 | Flowery | Alcohol C8 MG: 130.23 g/mol | 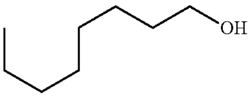 |
| 10 | Flowery | Alcohol C9 MG: 144.26 g/mol | 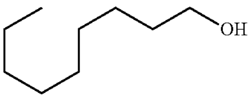 |
| 11 | Flowery | Alcohol C10 MG: 158.28 g/mol | 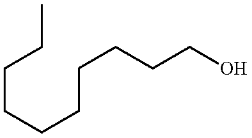 |

TABLE 2-continued

| No. | Fragrance-alcohol Group | Name Molecular weight (MG) | Structure |
|---|---|---|---|
| 14 | Flowery | Terpineol alpha MG: 154.25 g/mol | 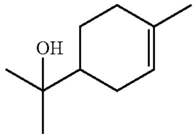 |
| 12 | Flowery | Tetrahydromyrcenol MG: 158.28 g/mol | 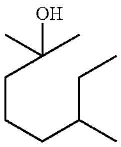 |

Particularly preferred is a perfume mixture, preferably a perfume oil, in which the one or more odorant alcohols having a floral odor note is/are selected from the group consisting of phenylethyl alcohol, linalool, citronellol, geraniol, nerol, ethyllinalool, tetrahydrolinalool, dihydromyrcenol and tetrahydromyrcenol.

Still further preferred is a perfume mixture, preferably a perfume oil, in which the one or more odorant alcohols is/are selected from the group consisting of odorant alcohols having green odor notes and from the group consisting of odorant alcohols having floral odor notes.

In a further preferred variant, the one or more odorant alcohols are selected from the group of odorant alcohols with green odor notes consisting of C6-alcohol, C7-alcohol, (Z)-3-hexenol (cis-3-hexenol), (E)-2-hexenol (trans-2-hexenol), (E/Z)-3-hexenol and (Z)-4-hexenol (cis-4-hexenol), and/or from the group of odorant alcohols with floral odor notes consisting of phenylethyl alcohol, linalool, citronellol, geraniol, nerol, ethyllinalool, tetrahydrolinalool, dihydromyrcenol, C8 alcohol, C9 alcohol, C10 alcohol, alpha-terpineol and tetrahydromyrcenol.

In a perfume mixture according to the invention, preferably a perfume oil, the skilled person will select the proportion of component (i), i.e. the proportion of 1,3-propanediol, in such a way that the desired effect of emphasizing and/or masking and/or diminishing an odor note or several odor notes of the one odorant alcohol or the several odorant alcohols is achieved. At the same time, he will take care not to use excessive amounts of the ingredient (i), i.e. of 1,3-propanediol, which could dominate the overall sensory impression of a perfume mixture. On the other hand, he will not provide only such a small amount of ingredient (i), i.e. 1,3-propanediol, that any highlighting or emphasising and/or masking or diminishing of odorous aspects of the one or more odorant alcohols is not or hardly perceptible.

Indeed, the 1,3-propanediol used according to the invention has the advantage that, when used, in particular according to the invention, it is already effective for the purposes of the present invention in such low concentrations in which no or at least no perceptible inherent odor is imparted. As a result, 1,3-propanediol can be combined with different fragrances as well as optionally further components of a perfume oil in order to produce particularly advantageous perfume mixtures or in order to perfume products with any desired fragrance.

Generally preferred is such a perfume mixture in which 1,3-propanediol is used in an effective amount sufficient to highlight or accentuate a pleasant odor note(s) of the one or more odorant alcohols and/or to mask or reduce an unpleasant odor note(s) of the one or more odorant alcohols.

By a sensory effective amount is meant a proportion of 1,3-propanediol sufficient to produce the above effects, i.e. highlighting and/or emphasizing a pleasant odor note and/or masking and/or reducing an unpleasant odor note in the perfume mixture.

Advantageously, the effective amounts of 1,3-propanediol are particularly suitable for highlighting or accentuating the natural freshness, vibrancy or floral odor note(s) of the one or more odorant alcohols in the perfume mixture and/or masking or reducing the greasy, technical or metallic odor notes of the one or more odorant alcohols in the perfume mixture.

In order to achieve the sensory effects described above, the 1,3-propanediol is added to the perfume mixture according to the invention in an amount of >10% by weight. Preferably, 1,3-propanediol is added to the perfume mixture according to the invention in an amount of >10% by weight to 90% by weight. Still more preferably, 1,3-propanediol is added to the perfume mixture according to the invention in an amount of from 20% by weight to 80% by weight. Still more preferably, 1,3-propanediol is added to the perfume mixture in an amount of from 30% by weight to 70% by weight. Still more preferably, 1,3-propanediol is added to the perfume mixture in an amount of from 40 wt %. to 60 wt %. Most preferably, 1,3-propanediol is added to the perfume mixture in an amount of ≥50% by weight. All amounts are based on the total weight of the perfume mixture.

Surprisingly, the sensory properties of the one odorant alcohol or the several odorant alcohols are positively influenced by combination with 1,3-propanediol in an amount of >10 wt. %. In general, impact and radiation increase with a higher proportion of odorant alcohol. From 20 wt. % onwards, the odor is less greasy and from 40 wt. % onwards, the odor is increasingly floral. Moreover, from 50 wt. % onwards, predominantly natural odorant mixtures can be achieved.

As a comparison of 10% solutions of the odorant alcohols in 1,3-propanediol with 10% solutions of the odorant alcohols in dipropylene glycol shows, the odorant alcohols in a 1,3-propanediol solution are perceived more strongly and with less unpleasant secondary notes than in a dipropylene glycol solution. The solutions in 1,3-propanediol appear more floral and natural. In individual cases, the sensory impression is shifted in the direction of more natural, fresher, more radiance, less musty, less artificial and less metallic. In individual cases, further sensory influences were also observed in the presence of 1,3-propanediol. Detailed odor descriptions can be found in the following Example 1, Table 3.

By varying the 1,3-propanediol concentration in the perfume mixture according to the invention, for example by increasing or decreasing the 1,3-propanediol content, the sensory properties of the perfume mixture and thus the sensory profile of the perfume mixture can be adjusted or varied. Preferably, the 1,3-propanediol content in the perfume mixture is adjusted to 90% by weight, 80% by weight, 70% by weight, 60% by weight, 50% by weight, 40% by weight, 30% by weight, 20% by weight and >10% by weight.

Depending on the 1,3-propanedilage content, the sensory profile of the perfume mixture according to the invention can be enhanced in favour of floral, natural, fresh, etc. notes and, on the other hand, the less unpleasant secondary notes can be repressed. For example, at a 90% concentration of 1,3-propanediol, the odorant alcohol linalool results in a juicy fruity sensory evaluation, at an 80% concentration of 1,3-propanediol it results in a clearer, brighter sensory evaluation, at a 60% concentration of 1,3-propanediol it results in a slightly floral fresher sensory evaluation, and at a 40% concentration of 1,3-propanediol it results in a floral clean sensory evaluation. Detailed odor descriptions as a function of 1,3-propanediol concentration can be found in Example 2, Table 4 below.

Varying the 1,3-propanediol concentration in the perfume mixture has the further advantage that perfume mixtures can be prepared whose natural or renewal content can be increased by the 1,3-propanediol content.

Even more preferred according to the present invention are perfume mixtures comprising either two, three, four, five or more different odorant alcohols selected from the group of odorant alcohols with green odor notes defined above and/or comprising two, three, four, five or more different odorant alcohols selected from the group of odorant alcohols with floral odor notes defined above, most preferably odorant alcohols selected from the group of odorant alcohols with green odor notes, which consists of C6-alcohol, C7-alcohol, (Z)-3-hexenol (cis-3-hexenol), (E)-2-hexenol (trans-2-hexenol), (E/Z)-3-hexenol and (Z)-4-hexenol (cis-4-hexenol), and/or from the group of odorant alcohols with floral odor notes, consisting of phenylethyl alcohol, linalool, citronellol, geraniol, nerol, ethyllinalool, tetrahydrolinalool, dihydromyrcenol, C8 alcohol, C9 alcohol, C10 alcohol, alpha-terpineol and tetrahydromyrcenol.

Preferably, perfume substance(s) from the group of perfume substance alcohols, in particular from the group of perfume substance alcohols with green notes and/or the group of perfume substance alcohols with floral notes, is/are present in the perfume substance mixture in a concentration of <90% by weight. Preferably, the one or more odorant alcohols from the group of odorant alcohols, in particular from the group of odorant alcohols with green notes and/or the group of odorant alcohols with floral notes, is/are present in the perfume mixture in a concentration of 10 to <90% by weight, in particular 11 to 90% by weight. Even more preferably, the one or more odorant alcohols from the group of odorant alcohols, in particular from the group of odorant alcohols with green notes and/or the group of odorant alcohols with floral notes, is/are present in the perfume mixture in a concentration of 20 to 80 wt. %. Even more preferably, the one or more odorant alcohols from the group of odorant alcohols, in particular from the group of odorant alcohols with green notes and/or the group of odorant alcohols with floral notes, is/are present in the perfume mixture in a concentration of 30 to 70% by weight. Even more preferably, the one or more odorant alcohols from the group of odorant alcohols, in particular from the group of odorant alcohols with green notes and/or the group of odorant alcohols with floral notes, is/are present in the perfume mixture in a concentration of 40 to 60% by weight. Most preferably, the one or more odorant(s) from the group of odorant alcohols, in particular from the group of odorant alcohols with green notes and/or the group of odorant alcohols with floral notes, is/are present in the odorant mixture in a concentration of 50% by weight, in particular <51% by weight. All quantities are based on the total weight of the perfume mixture.

In the context of the present invention, a perfume mixture is particularly preferred in which the quantity ratio of 1,3-propanediol to total quantity of odorant alcohol(s) is 50:50, preferably 40:60, still more preferably 20:80 and most preferably 10:90, or in particular in the perfume mixture according to the invention, the quantity ratio of 1,3-propanediol to total quantity of odorant alcohol(s) with green odor note is 50:50, preferably 40:60, still more preferably 20:80 and most preferably 10:90, or in particular in the perfume mixture according to the invention the quantity ratio of 1,3-propanediol to total quantity of odorant alcohol(s) with a floral odor note is 50:50, preferably 40:60, still more preferably 20:80 and most preferably 10:90.

In an alternatively preferred embodiment of the present invention, ingredients (i) and (ii) are present in the perfume mixture in an amount of from 1 to 100% by weight combined, preferably in an amount of from 10 to 90% by weight combined, more preferably in an amount of from 20 to 80 and most preferably in an amount of from 40 to 60% by weight based on the total weight of the perfume mixture.

Particularly preferred ratios according to the invention are also apparent from the embodiments described further below and, in particular, from the accompanying examples.

Perfume mixtures according to the invention are usually liquid at 25° C. and 1013 hPa and are generally homogeneous solutions.

In addition to the particular olfactory advantages, mention should also be made of the excellent material properties of the perfume mixture according to the invention, such as solubility in conventional cosmetic solvents, compatibility with other constituents of such products and the toxicological harmlessness of the perfume mixture according to the invention, which underline the particular suitability for the purposes of use described below.

A perfume mixture according to the invention may preferably contain, in addition to ingredients (i) and (ii) as described above, one or more further (usual) active ingredients or functional ingredients, also one or more further solvents not meeting the above criteria of ingredient (i) or fragrances not meeting the above criteria of ingredient (ii), making the sum to 100% by weight in the perfume mixture, preferably in the perfume oil.

Perfume mixtures according to the invention, in particular perfume oils, can be used in liquid form undiluted or diluted with a solvent for perfuming. Suitable and preferred solvents for this purpose are in particular ethanol, glycerol, 1,2-propylene glycol, 1,2-butylene glycol, dipropylene glycol, diethyl phthalate, triethyl citrate, isopropyl myristate and triacetin.

These perfume mixtures may contain up to 90% by weight, preferably from about 5% to about 70% by weight, more preferably from about 10% to about 50% by weight, and particularly preferably from about 15% to about 25% by weight of said solvents.

In a preferred alternative, the perfume mixtures according to the invention, in particular perfume oils, comprise synthetic or natural carrier substances which are preferably neutral in taste and odor, in particular carrier oils which contain the perfume substances in a highly concentrated form and optionally perfumery solvents and/or excipients.

Furthermore, the perfume mixtures according to the invention, preferably perfume oils, are adsorbed on a carrier which provides both a fine distribution of the perfumes contained therein in the product and a controlled release during application. Such carriers may be porous inorganic materials such as light sulfate, silica gels, zeolites, gypsums, clays, clay granules, aerated concrete, etc., or organic materials such as woods, cellulose-based materials, sugars, dextrins (e.g., maltodextrin) or plastics such as PVC, polyvinyl acetates or polyurethanes. The combination of the perfume mixture and carrier according to the invention represents an exemplary product according to the invention.

In an alternative preferred embodiment, the perfume mixtures according to the invention, preferably perfume oils, are present in microencapsulated or spray-dried form, or are present as inclusion complexes or as extrusion products, in order to be added in this form, for example, to a product to be perfumed.

The microencapsulation of the perfume compositions according to the invention, preferably perfume oils, can be carried out, for example, by the so-called coacervation process using capsule materials made, for example, of polyurethane-like substances or soft gelatine. The spray-dried perfume or aroma compositions may be prepared, for example, by spray-drying an emulsion or dispersion containing the perfume mixture according to the invention, wherein modified starches, proteins, dextrin and vegetable gums may preferably be used as carriers. Inclusion complexes can be prepared, for example, by incorporating dispersions of a perfume mixture according to the invention and cyclodextrins or urea derivatives in a suitable solvent, for example water. Extrusion products can be obtained by fusing a perfume mixture according to the invention, preferably a perfume oil, with a suitable waxy substance and by extrusion followed by solidification, optionally in a suitable solvent, e.g. isopropanol.

If necessary, the properties of such modified perfume mixture preparations can be further optimized by so-called "coating" with suitable materials with a view to a more specific release of fragrance, for which purpose waxy plastics such as, for example, polyvinyl alcohol are preferably used. The resulting products comprising the perfume mixture according to the invention, preferably perfume oils, in turn constitute products according to the invention.

Examples of further additional fragrance materials which can in principle advantageously be used as a component of a perfume mixture according to the invention, in particular of a perfume oil, can be found, for example, in "S. Arctander, Perfume and Flavor Chemicals, Volumes I and II, Montclair, N.J., 1969, self-published" or "H. Surburg and J. Panten, Common Fragrance and Flavor Materials, 6th edition, Wiley-VCH, Weinheim, 2016" as well as, in particular, the further fragrances explicitly mentioned in US 2008/0070825 which are not already part of the components (ii) of the perfume mixture according to the invention, preferably of a perfume oil.

Usually, fragrances are not used in binary or ternary mixtures, but as a component of sophisticated complex mixtures which may contain two, three, four, five, ten, or preferably a much higher number of fragrances in sometimes very small quantities to give a particularly rounded odor profile.

In a preferred further development of the present invention, the perfume mixture described therefore contains any desired number of further odorants which do not fall within the definition of odorant alcohols (ii) according to the invention and which are selected from the group formed by: (1) hydrocarbons; (2) aliphatic alcohols; (3) aliphatic aldehydes and their acetals; (4) aliphatic ketones and their oximes; (5) aliphatic sulfur-containing compounds; (6) aliphatic nitriles; (7) esters of aliphatic carboxylic acids; (8) acyclic terpene alcohols; (9) acyclic terpene aldehydes and ketones; (10) cyclic terpene alcohols; (11) cyclic terpene aldehydes and ketones; (12) cyclic alcohols; (13) cycloaliphatic alcohols; (14) cyclic and cycloaliphatic ethers; (15) cyclic and macrocyclic ketones; (16) cycloaliphatic aldehydes; (17) cycloaliphatic ketones; (18) esters of cyclic alcohols; (19) esters of cycloaliphatic alcohols; (20) esters of cycloaliphatic carboxylic acids; (21) araliphatic alcohols;

(22) esters of araliphatic alcohols and aliphatic carboxylic acids; (23) araliphatic ethers; (24) aromatic and araliphatic aldehydes; (25) aromatic and araliphatic ketones; (26) aromatic and araliphatic carboxylic acids and esters thereof; (27) nitrogen-containing aromatic compounds; (28) phenols, phenyl ethers and phenyl esters; (29) heterocyclic compounds; (30) lactones; and mixtures thereof.

In particular, the following odoriferous substances may be mentioned:

Extracts from natural raw materials: This group represents essential oils, concretes, absolues, resins, resinoids, balsams, tinctures such as ambergris oil; Amyris oil; Angelica seed oil; Angelica root oil; Anise oil; Valerian oil; Basil oil; Tree moss absolue; Bay oil; Mugwort oil; Benzoeresin; Bergamot oil; Beeswax absolue; Birch tar oil; Bitter almond oil; Savory oil; Bucco leaf oil; Cabreuva oil; Cade oil; Calmus oil; Camphor oil; Cananga oil; Cardamom oil; Cascarilla oil; Cassia oil; Cassie-absolue; Castoreum-absolue; Cedar leaf oil; Cedarwood oil; Cistus oil; Citronella oil; Citron oil; Copaiva balsam; Copaiva balsam oil; Coriander oil; Costus root oil; Cumin oil; Cypress oil; Davana oil; Dill herb oil; Dill seed oil; Eau de brouts absolute; Oak moss absolute; Elemi oil; Tarragon oil; Eucalyptus citriodora oil; Eucalyptus oil; Fennel oil; Spruce needle oil; Galbanum oil; Galbanum resin; Geranium oil; Grapefruit oil; Guaiac wood oil; Gurjun balsam; Gurjun balsam oil; Helichrysum absolute; Helichrysum oil; Ginger oil; Iris root absolute; Iris root oil; Jasmine absolute; Calamus oil; Camomile oil blue; Camomile oil Roman; Carrot seed oil; Cascarilla oil; Pine needle oil; Curly mint oil; Caraway seed oil; Labdanum oil; Labdanum absolute; Labdanum resin; Lavandin absolute; Lavandin oil; Lavender absolute; Lavender oil; Lemongrass oil; Lovage oil; Lime oil distilled; Lime oil pressed; Linaloe oil; Litsea cubeba oil; Bay leaf oil; Mace oil; Marjoram oil; Mandarin oil; Masso bark oil; Mimosa absolue; Musk grain oil; Musk tincture; Muscat oil; Myrrh absolute; Myrrh oil; Myrtle oil; Clove leaf oil; Clove flower oil; Neroli oil; Olibanum absolute; Olibanum oil; Opopanax oil; Orange flower absolute; Orange oil; Origanum oil; Palmarosa oil; Patchouli oil; Perilla oil; Perubalsam oil; Parsley leaf oil; Parsley seed oil; Petitgrain oil; Peppermint oil; Pepper oil; Allspice oil; Pine oil; Poley oil; Rose absolue; Rosewood oil; Rose oil; Rosemary oil; Sage oil Dalmatian; Sage oil Spanish; Sandalwood oil; Celery seed oil; Spicy lavender oil; Star anise oil; Styrax oil; Tagetes oil; Fir needle oil; Tea tree oil; Turpentine oil; thyme oil; tolu balsam; tonka absolute; tuberose absolute; vanilla extract; violet leaf absolute; verbena oil; vetiver oil; juniper berry oil; wine yeast oil; wormwood oil; wintergreen oil; ylang oil; hyssop oil; civet absolute; cinnamon leaf oil; cinnamon bark oil; and fractions thereof, or ingredients isolated therefrom.

Single fragrances: Single fragrances can be divided into a variety of classes, namely:

- Hydrocarbons, such as 3-carene;α β-pinene; α-terpinene; γ-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;
- Aliphatic alcohols such as 3-octanol; 2,6-dimethylheptanol; 2-methyl-2-heptanol; 2-methyl-2-octanol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxy octan-2-ol; 9-decenol; 10-undecenol; 4-methyl-3-decen-5-ol;
- Aliphatic aldehydes and their acetals such as hexanal; heptanal; octanal; nonanal; decanal; undecanal; dodecanal; tridecanal; 2-methyloctanal; 2-methyl-nonanal; (E)-2-hexenal; (Z)-4-heptenal; 2,6-dimethyl-5-heptenal; 10-undecenal; (E)-4-decenal; 2-dodecenal;2,6,10-trimethyl-9-undecenal; 2,6,10-trimethyl-5,9-undecadienal; heptanal diethyl acetal; 1,1-dimethoxy-2,2,5-trimethyl-4-hexene; citronellyloxyacetaldehyde; 1-(1-methoxy-propoxy)-(E/Z)-3-hexene;
- Aliphatic ketones and their oximes such as 2-heptanone; 2-octanone; 3-octanone; 2-nonanone; 5-methyl-3-heptanone; 5-methyl-3-heptanonoxime; 2,4,4,7-tetramethyl-6-octen-3-one; 6-methyl-5-hepten-2-one;
- Aliphatic sulfur-containing compounds such as 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthen-8-thiol;
- Aliphatic nitriles such as 2-nonenoic acid nitrile; 2-undecenoic acid nitrile; 2-tridecenoic acid nitrile; 3,12-tridecadienoic acid nitrile; 3,7-dimethyl-2,6-octadienoic acid nitrile; 3,7-dimethyl-6-octenoic acid nitrile;
- Esters of aliphatic carboxylic acids such as (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate, isoamyl butyrate; hexyl butyrate; (E)- and (Z)-3-hexenyl isobutyrate; Hexyl crotonate; Ethyl isovalerate; Ethyl 2-methyl pentanoate; Ethyl hexanoate; Allyl hexanoate; Ethyl heptanoate; Allyl heptanoate; Ethyl octanoate; ethyl (E,Z)-2,4-decadienoate; methyl 2-octinate; methyl 2-noninate; allyl 2-isoamyloxyacetate; methyl 3,7-dimethyl-2,6-octadienoate; 4-methyl-2-pentyl crotonate;
- Acyclic terpene alcohols such as lavadulol; nerolidol; farnesol; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; and their formates, acetates, propionates, isobutyrates, butyrates, isovalerianates, pentanoates, hexanoates, crotonates, tiglinates and 3-methyl-2-butenoates;
- Acyclic terpene aldehydes and ketones such as geranial; neral; citronellal; 7-hydroxy-3,7-dimethyloctanal; 7-methoxy-3,7-dimethyloctanal; 2,6,10-trimethyl-9-undecenal; geranylacetone; and the dimethyl and diethylacetals of geranial, neral, 7-hydroxy-3,7-dimethyloctanal;
- Cyclic terpene alcohols such as menthol; isopulegol; terpinenol-4; menthan-8-ol; menthan-1-ol; menthan-7-ol; borneol; isoborneol; linalool oxide; nopol; cedrol; ambrinol; vetiverol; guaiaol; and their formates, acetates, propionates, isobutyrates, butyrates, isovalerianates, pentanoates, hexanoates, crotonates, tiglinates and 3-methyl-2-butenoates;
- Cyclic terpene aldehydes and ketones such as menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-Trimethyl-2-cyclohexen-1-yl)-2-buten-1-on; 1,3,4,6,7,8a-Hexahydro-1,1,5,5-tetramethyl-2H-2,4a-methanonaphthalen-8(5H)-on;2-Methyl-4-(2,6,6-trimethyl-1-cyclohexen-1-yl)-2-butenal; nootkatone;

dihydronootkatone; 4,6,8-megastigmatrien-3-one; alpha-sinensal; beta-sinensal; acetylated cedarwood oil (methylcedrylketone);

Cyclic alcohols such as 4-tert-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

Cycloaliphatic alcohols such as alpha,3,3-trimethylcyclohexylmethanol;1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

Cyclic and cycloaliphatic ethers such as cineol; cedryl methyl ether; cyclododecyl methyl ether; 1,1-dimethoxycyclododecane; (ethoxymethoxy)cyclododecane; alpha-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo [10.1.0] tri deca-4,8-diene; rose oxide; 2-(2,4-dimethyl-3-cyclohexen-1-yl)-5-methyl-5-(1-methylpropyl)-1,3-dioxane;

Cyclic and macrocyclic ketones such as 4-tert.butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert.-pentylcyclohexanone; 5-cyclohexadecen-1-one; 6,7-dihydro-1,1,2,3,3-pentamethyl-4(5H)-indanone; 8-cyclohexadecen-1-one; 9-cycloheptadecen-1-one; cyclopentadecanone; cyclohexadecanone;

Cycloaliphatic aldehydes such as 2,4-dimethyl-3-cyclohexenecarbaldehyde; 2-methyl-4-(2,2,6-trimethyl-cyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde;

Cycloaliphatic ketones such as 1-(3,3-Dimethylcyclohexyl)-4-penten-1-on; 2,2-Dimethyl-1-(2,4-dimethyl-3-cyclohexen-1-yl)-1-propanon; 1-(5,5-Dimethyl-1-cyclo hexen-1-yl)-4-penten-1-on; 2,3,8,8-tetramethyl-1,2,3,4,5,6,7,8-octahydro-2-naphtalenyl methyl ketone; methyl-2,6,10-trimethyl-2,5,9-cyclododecatrienyl ketone; tert.-butyl-(2,4-dimethyl-3-cyclohexen-1-yl)ketone;

Esters of cyclic alcohols such as 2-tert-butyl cyclohexyl acetate; 4-tert-butyl cyclo hexyl acetate; 2-tert-pentyl cyclohexyl acetate; 4-tert-pentyl cyclohexyl acetate; 3,3,5-trimethyl cyclohexyl acetate; decahydro-2-naphthyl acetate;2-cyclopentylcyclo-pentylcro tonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5, resp. 6-indenyl acetate; 4,7-methano-3a,4,5,6,7,7a-hexahydro-5, or 6-indenyl propionate; 4,7-methano-3a,4,5,6,7,7a-hexahydro-5, or 6-indenyl isobutyrate; 4,7-methanooctahydro-5, or 6-indenyl acetate;

Esters of cycloaliphatic alcohols such as 1-cyclohexylethyl crotonate;

Esters of cycloaliphatic carboxylic acids such as allyl 3-cyclohexyl propionate; allyl cyclohexyloxy acetate; cis- and trans-methyl dihydrojasmonate; cis- and trans-methyl jasmonate; methyl 2-hexyl-3-oxocyclopentane carboxylate; ethyl 2-ethyl-6,6-dimethyl-2-cyclohexenecarboxylate; ethyl 2,3,6,6-tetramethyl-2-cyclohexene carboxylate; ethyl 2-methyl-1,3-dioxolane-2-acetate;

Araliphatic alcohols such as benzyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenyl propanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

Esters of araliphatic alcohols and aliphatic carboxylic acids such as benzyl acetate; benzyl propionate; benzyl isobutyrate; benzyl isovalerianate; 2-phenyl ethyl acetate; 2-phenylethyl propionate; 2-phenylethyl isobutyrate; 2-phenylethyl iso-valerianate; 1-phenylethyl acetate; alpha-trichloromethyl benzyl acetate; alpha,alpha-dimethylphenyl ethyl acetate; alpha,alpha-dimethylphenyl ethyl butyrate; cinnamyl acetate; 2-phenoxyethyl isobutyrate; 4-methoxybenzyl acetate;

Araliphatic ethers such as 2-phenylethyl methyl ether; 2-phenylethyl isoamyl ether; 2-phenylethyl-1-ethoxyethyl ether; phenylacetaldehyde dimethylacetal; phenylacetaldehyde diethylacetal; hydratropaaldehyde dimethylacetal; phenylacetaldehydeglycerolacetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

Aromatic and araliphatic aldehydes such as benzaldehyde; phenylacetaldehyde; 3-phenylpropanal; hydratropaaldehyde; 4-methylbenzaldehyde; 4-methylphenyl acetaldehyde; 3-(4-ethylphenyl)-2,2-dimethylpropanal; 2-methyl-3-(4-isopropyl phenyl) propanal; 2-methyl-3-(4-tert.-butylphenyl)propanal; 2-methyl-3-(4-isobutyl phenyl)propanal; 3-(4-tert.-butylphenyl)propanal; cinnamaldehyde; alpha-butyl cinnamaldehyde; alpha-amyl cinnamaldehyde; alpha-hexyl cinnamaldehyde; 3-methyl-5-phenylpentanal; 4-methoxy benzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde 2-methyl-3-(4-methoxy phenyl)propanal; 2-methyl-3-(4-methylenedioxyphenyl)propanal;

Aromatic and araliphatic ketones such as acetophenone; 4-methylaceto phenone; 4-methoxyacetophenone; 4-tert.butyl-2,6-dimethylacetophenone; 4-phenyl-2-butanone; 4-(4-hydroxyphenyl)-2-butanone; 1-(2-naphthalenyl)ethanone;2-benzofuranyl ethanone; (3-methyl-2-benzofuranyl)ethanone; benzophenone; 1,1,2,3,6-hexamethyl-5-indanyl methyl ketone; 6-tert-.butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

Aromatic and araliphatic carboxylic acids and their esters such as benzoic acid; phenylacetic acid; methyl benzoate; ethyl benzoate; hexyl benzoate; benzyl benzoate; methyl phenyl acetate; ethyl phenyl acetate; geranyl phenyl acetate; phenyl ethyl phenyl acetate; methyl cinnamate; ethyl cinnamate; benzyl cinnamate; phenyl ethyl cinnamate; cinnamyl cinnamate; allyl phenoxy acetate; methyl salicylate; isoamyl salicylate; hexyl salicylate; cyclohexyl salicylate; cis-3-hexenyl salicylate; benzyl salicylate; phenyl ethyl salicylate; methyl 2,4-dihydroxy-3,6-dimethylbenzoate; ethyl 3-phenyl glycidate; ethyl 3-methyl-3-phenylglycidate;

Nitrogen-containing aromatic compounds such as 2,4,6-trinitro-1,3-dimethyl-5-tert-butylbenzene; 3,5-dinitro-2,6-dimethyl-4-tert.butylacetophenone; cinnamic acid nitrile; 3-methyl-5-phenyl-2-pentenoic acid nitrile; 3-methyl-5-phenylpentanoic acid nitrile; methyl anthranilate; methyl N-methyl anthranilate; Schiff bases of methyl anthranilate with 7-hydroxy-3,7-dimethyloctanal, 2-methyl-3-(4-tert.-butylphenyl)propanal or 2,4-dimethyl-3-cyclohexenecarbaldehyde; 6-isopropylquinoline; 6-isobutylquinoline; 6-sec-butylquinoline;2-(3-phenylpropyl)pyridine; indole; scatole; 2-methoxy-3-isopropylpyrazine; 2-isobutyl-3-methoxypyrazine;

Phenols, phenyl ethers and phenyl esters such as estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimeth oxybenzene; eugenyl acetate; 2-methoxy-4-methylphenol; 2-ethoxy-5-(1-propenyl) phenol; p-cresyl phenyl acetate;

Heterocyclic compounds such as 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

Lactones such as 1,4-octanolide; 3-methyl-1,4-octanolide; 1,4-nonanolide; 1,4-decaneolide; 8-decene-1,4-olide; 1,4-undecanolide; 1,4-dodecanolide; 1,5-decanolide; 1,5-dodecanolide;4-methyl-1,4-decanolide; 1,15-pentadecanolide; cis- and trans-11-pentadecene-1,15-olide; cis- and trans-12-pentadecene-1,15-olide; 1,16-hexadecanolide; 9-hexadecene-1,16-olide; 10-oxa-1,16-hexadecanolide; 11-oxa-1,16-hexadecanolide; 12-oxa-1,16-hexadecanolide; ethylene-1,12-dodecanedioate; ethylene-1,13-tridecanedioate; coumarin; 2,3-dihydrocoumarin; octahydrocoumarin;

as well as any mixtures of the above-mentioned fragrances.

In a second aspect, the present invention relates to a process for preparing a perfume mixture. In the method according to the present invention, the ingredients (i) and (ii) of the perfume mixture are first provided and then brought into contact with each other and mixed to obtain the non-aqueous perfume mixture according to the present invention.

As regards the ingredients (i) and (ii), their preferred or alternative embodiments, their mixing and quantity ratios and their beneficial effects, reference is made to the above detailed description in connection with the perfume mixture according to the invention, which is equally valid for the process according to the second aspect of the invention.

In the process for preparing the perfume mixture according to the invention, the 1,3-propanediol is added to the odorant alcohol or the plurality of odorant alcohols in an amount of >10% by weight. Preferably, 1,3-propanediol is added in an amount of >10% by weight to 90% by weight. Even more preferably, 1,3-propanediol is added in an amount of from 20% to 80% by weight. Still more preferably, 1,3-propanediol is added to the perfume mixture in an amount of from 30% by weight to 70% by weight. Still more preferably, 1,3-propanediol is added to the perfume mixture in an amount of 40 wt. % to 60 wt. %. Most preferably, 1,3-propanediol is added to the perfume mixture in an amount of 50 wt %. All amounts are based on the total weight of the perfume mixture.

In a further preferred variant of the process according to the invention resulting in a perfume mixture according to the invention, preferably a perfume oil, the quantity ratio of 1,3-propanediol to total quantity of odorant alcohol(s) is 50:50, preferably 40:60, still more preferably 20:80 and most preferably 10:90, or in particular in the perfume mixture according to the invention the quantity ratio of 1,3-propanediol to total quantity of odorant alcohol(s) with green odor note is 50:50, preferably 40:60, even more preferably 20:80 and most preferably 10:90, or in particular in the perfume mixture according to the invention the ratio of 1,3-propanediol to the total amount of odorant alcohol(s) with a floral odor note is 50:50, preferably 40:60, even more preferably 20:80 and most preferably 10:90.

In an alternative preferred variant of the method according to the present invention, the ingredients (i) and (ii) are present in the perfume mixture, preferably a perfume oil, in an amount of from 1 to 100% by weight together, preferably in an amount of from 10 to 90% by weight together, more preferably in an amount of from 20 to 80 and most preferably in an amount of from 40 to 60% by weight, based on the total weight of the perfume mixture.

According to a third aspect, the present invention relates to a method for modifying the sensory properties of one or more odorant alcohols, comprising the steps of:

Mixing an odorant alcohol or alcohols with an effective amount of >10% by weight of 1,3-propanediol in order to accentuate or enhance a pleasant odor note or all the pleasant odor notes of an odorant alcohol or of several odorant alcohols;

and/or to mask or reduce an unpleasant odor note or all unpleasant odor notes of one or more odorant alcohols.

Surprisingly, the method according to the third aspect of the present invention can be used to modify the sensory properties of one or more odorant alcohols using 1,3-propanediol.

In particular, a pleasant odor note or all pleasant odor notes, for example more radiance, natural freshness or floral odor note(s) of an odorant alcohol or several odorant alcohols, can be emphasized or enhanced by the aforementioned method when 1,3-propanediol is used in an effective amount as described above.

In an analogous manner, an unpleasant odor note or all unpleasant odor notes, for example musty, greasy, technical or metallic odor note(s) of an odorant alcohol or several odorant alcohols, can preferably be masked or reduced by the aforementioned method when 1,3-propanediol is used in an effective amount as described above.

The one, more or all of the odorant alcohol(s) whose odor properties are improved by the use of 1,3-propanediol according to the invention is preferably one or more odorant alcohol(s) with a green odor note or one or more odorant alcohol(s) with a floral odor note.

Generally preferred is/are the one, more or all of the unpleasant and/or pleasant smelling, green smelling odorant alcohol(s) selected from the group consisting of odorant alcohols having a molecular weight in the range of from 100 g/mol to 190 g/mol, preferably in the range of from 100 g/mol to 158 g/mol.

In a preferred embodiment, the one or more green olfactory alcohols are selected from the group consisting of C6 alcohol, C7 alcohol, (Z)-3-hexenol (cis-3-hexenol), (E)-2-hexenol (trans-2-hexenol), (E/Z)-3-hexenol, and (Z)-4-hexenol (cis-4-hexenol).

Alternatively preferred is/are the one, more or all of the unpleasant and/or pleasant-smelling odorant alcohol(s) having a floral odor selected from the group consisting of odorant alcohols having a molecular weight in the range of from 120 g/mol to 200 g/mol, preferably in the range of from 122 to 168 g/mol.

In a preferred embodiment, the one or more odorant alcohols having a floral odor are selected from the group consisting of phenylethyl alcohol, linalool, citronellol, geraniol, nerol, ethyllinalool, tetrahydrolinalool, dihydromyrcenol, C8 alcohol, C9 alcohol, C10 alcohol, alpha-terpineol and tetrahydromyrcenol.

Even more preferred are either two, three, four, five or more different odorant alcohols selected from the group of odorant alcohols with green odor note consisting of C6 alcohol, C7 alcohol, (Z)-3-hexenol (cis-3-hexenol), (E)-2-hexenol (trans-2-hexenol), (E/Z)-3-hexenol and (Z)-4-hexenol (cis-4-hexenol), and/or from the group of odorant alcohols with a floral odor, which consists of phenylethyl alcohol, linalool, citronellol, geraniol, nerol, ethyllinalool, tetrahydrolinalool, dihydromyrcenol, C8 alcohol, C9 alcohol, C10 alcohol, alpha-terpineol and tetrahydromyrcenol.

As regards the ingredients (i) and (ii), their preferred or alternative embodiments and their mixing and quantity ratios, as well as their beneficial effects, reference is made to the above detailed description in connection with the perfume mixture according to the invention, which is equally valid for the process according to the third aspect of the invention.

Surprisingly, the sensory properties of the one or more odorant alcohols are positively influenced by combination with an effective amount of >10% by weight of 1,3-propanediol.

Most preferably, the sensory properties of the one odorant alcohol or the plurality of odorant alcohols are even more positively influenced when 1,3-propanediol is used in an amount of >10 wt % to 90 wt %. Most preferably, the sensory properties of the one odorant alcohol or the plurality of odorant alcohols are positively influenced when 1,3-propanediol is used in an amount of 20% by weight to 80% by weight. Even more preferably, the sensory properties of the one odorant alcohol or the plurality of odorant alcohols are positively influenced when 1,3-propanediol is used in an amount of from 30 wt. % to 70 wt. %. Even more preferably, the sensory properties of the one odorant alcohol or the plurality of odorant alcohols are positively influenced when 1,3-propanediol is used in an amount of from 40 wt % to 60 wt %. Most preferably, the sensory properties of the one odorant alcohol or the plurality of odorant alcohols are positively influenced when 1,3-propanediol is used in an amount of >50% by weight. All amounts are based on the total weight of the perfume mixture.

In individual cases, the sensory impression is shifted in the direction of more natural, fresher, more radiant, less musty, less artificial and less metallic. In individual cases, other sensory influences were also observed in the presence of 1,3-propanediol.

The modification of the sensory properties of the odorant alcohols according to the invention as a function of the 1,3-propanediol concentration is shown by way of example in Table 4 below.

Particularly advantageous effects, i.e. the accentuation or emphasis of pleasant odor notes of an odorant alcohol or the masking or reduction of unpleasant odor notes of an odorant alcohol, are achieved when in the process according to the invention for modifying the sensory properties of an odorant alcohol or several odorant alcohols according to the third aspect of the invention the quantity ratio of 1,3-propanediol to total quantity of odorant alcohol(s) is 50:50, preferably 40:60, even more preferably 20:80 and most preferably 10:90, or in particular the quantity ratio of 1,3-propanediol to total quantity of odorant alcohol(s) with green odor note is 50:50, preferably 40:60, even more preferably 20:80 and most preferably 10:90, or in particular the quantity ratio of 1,3-propanediol to total quantity of odorant alcohol(s) with floral odor note is 50:50, preferably 40:60, even more preferably 20:80 and most preferably 10:90.

In another aspect, the present invention also relates to the use of >10% by weight of 1,3-propanediol for modifying the sensory properties of one or more odorant alcohols, in particular

- to emphasise or enhance a pleasant odor note or all the pleasant odor notes of one or more odoriferous alcohols; and/or
- for masking or reducing an unpleasant odor note or all unpleasant odor notes of one or more odorant alcohols.

Surprisingly, the presence of 1,3-propanediol causes certain olfactory aspects of the one or more odorant alcohols to be modified, i.e., emphasized or highlighted and/or masked or diminished.

Surprisingly, the use of 1,3-propanediol in combination with one or more odorant alcohol(s) has the particular effect of emphasizing or highlighting, i.e. enhancing, the positive, i.e. pleasant odor notes, such as radiance, natural freshness or the floral odor notes of an odorant alcohol or all odorant alcohols, and/or masking or reducing the negative, i.e. unpleasant odor notes, such as musty, fatty, technical or metallic odor notes.

With regard to the terms “highlighting” or “emphasizing” or “masking” or “diminishing”, reference is made to the above explanations in connection with the perfume mixture according to the invention, which are equally valid in connection with the use of 1,3-propanediol for modifying the sensory properties of an odorant alcohol, so that it is unnecessary to repeat them.

The 1,3-propanediol to be used according to the invention is furthermore advantageously easily accessible or producible, exhibits a high degree of efficacy even in low concentrations, in particular in concentrations at which 1,3-propanediol has no or at least only a barely perceptible inherent odor, is largely or completely colorless, has a high degree of stability in various mixtures or preparations, and exhibits no toxic and/or allergenic effect towards humans.

In addition, 1,3-propanediol has an antibacterial effect, a property that gives the resulting products microbial stability and thus shelf life.

1,3-Propanediol also has the advantage that in its use, in particular a use according to the invention, it can be combined with different fragrances and usual components of a perfume mixture to perfume products with any desired fragrance. Consequently, a wide range of fragrance types can be offered to consumers by the present invention.

According to a preferred variant of the present invention, 1,3-propanediol is particularly suitable for masking or reducing, in particular for reducing, one or more unpleasant odor notes of an odorant alcohol or several odorant alcohols. The unpleasant smelling substances mentioned herein may have other sensory qualities, including odor qualities, which are generally not unpleasant. Thus, as used herein, unpleasant smelling substances are generally understood to be those that elicit one or more unpleasant olfactory sensations or notes, whether as a primary odor or as a secondary/subordinate odor note. In particular, the unpleasant smelling substances described herein may also be those odoriferous substances which are primarily perceived as pleasant-smelling substances, but which also have an unpleasant metallic, greasy and/or technical odor note which it is preferable to reduce according to the invention.

The same applies analogously to the pleasant-smelling substances described herein. In the context of the present text, pleasant-smelling substances are generally understood to be substances that evoke one or more pleasant odor impressions or odor notes, whether as a primary odor or as a secondary/subordinate odor note.

As a result, in the context of the present invention, for example, both an unpleasant odor note of a particular (unpleasant-smelling) odorant alcohol can be masked or reduced, and a pleasant odor note of the same (also pleasant-smelling) odorant alcohol can be enhanced.

The one, more or all of the odorant alcohol(s) whose odor properties are improved by the use of 1,3-propanediol according to the invention is preferably one or more odorant alcohol(s) with a green odor note or one or more odorant alcohol(s) with a floral odor note.

Generally preferred is/are the one, more or all of the unpleasant and/or pleasant smelling, green smelling odorant alcohol(s) selected from the group consisting of odorant alcohols having a molecular weight in the range of from 100 g/mol to 190 g/mol, preferably in the range of from 100 g/mol to 158 g/mol.

In a preferred embodiment, the one or more green-smelling odorant alcohols are selected from the group consisting of C6 alcohol, C7 alcohol, (Z)-3-hexenol (cis-3-hexenol), (E)-2-hexenol (trans-2-hexenol), (E/Z)-3-hexenol, and (Z)-4-hexenol (cis-4-hexenol).

Alternatively preferred is/are the one, more or all of the unpleasant and/or pleasant-smelling odorant alcohol(s) having a floral odor selected from the group consisting of odorant alcohols having a molecular weight in the range of from 120 g/mol to 200 g/mol, preferably in the range of from 122 to 168 g/mol.

In a preferred embodiment, the one or more odorant alcohols having a floral odor are selected from the group consisting of phenylethyl alcohol, linalool, citronellol, geraniol, nerol, ethyllinalool, tetrahydrolinalool, dihydromyrcenol, C8 alcohol, C9 alcohol, C10 alcohol, alpha-terpineol and tetrahydromyrcenol.

Even more preferred are either two, three, four, five or more different odorant alcohols selected from the group of odorant alcohols with green odor note consisting of C6-alcohol, C7-alcohol, (Z)-3-hexenol (cis-3-hexenol), (E)-2-hexenol (trans-2-hexenol), (E/Z)-3-hexenol and (Z)-4-hexenol (cis-4-hexenol), and/or from the group of odorant alcohols with a floral odor, which consists of phenylethyl alcohol, linalool, citronellol, geraniol, nerol, ethyllinalool, tetrahydrolinalool, dihydromyrcenol, C8 alcohol, C9 alcohol, C10 alcohol, alpha-terpineol and terahydromyrcenol.

Surprisingly, the sensory properties of the one or more odorant alcohols are positively influenced by combination with an effective amount of 1,3-propanediol. In individual cases, the sensory impression is shifted in the direction of more natural, fresher, more radiance, less musty, less artificial and less metallic, whereby in individual cases further sensory influences were also observed in the presence of 1,3-propanediol.

Even more preferred are comprising two, three, four, five or more different odorant alcohols from the group of odorant alcohols with green odor notes and/or comprising two, three, four, five or more different odorant alcohols from the group of odorant alcohols with floral odor notes.

In the use according to the invention according to the fourth aspect, the person skilled in the art will select the proportion of 1,3-propanediol in such a way that the desired effect of emphasizing and/or highlighting and/or masking and/or diminishing an odor note or several odor notes of the perfume compound(s) is achieved. At the same time, he will take care not to use too large a quantity of ingredient (i), i.e. of 1,3-propanediol, which could dominate the overall sensory impression of a perfume mixture. On the other hand, he will not provide only such a small amount of ingredient (i), i.e. 1,3-propanediol, that an accentuation and/or masking and/or diminution of odorous aspects of the one or more odorant alcohols is not or hardly perceptible.

Also, particularly suitable for the purposes of the present invention is a use wherein the amount of 1,3-propanediol used to emphasize or highlight and/or to mask or diminish is not sufficient to impart an inherent odor. Indeed, the 1,3-propanediol used according to the invention has the advantage that when used, in particular according to the invention, it is effective for the purposes of the present invention even at such low concentrations at which no, or at least no, perceptible inherent odor is imparted. As a result, 1,3-propanediol can be combined with different fragrances as well as optionally further components of a perfume oil in order to produce particularly advantageous perfume mixtures or in order to perfume products with any desired fragrance.

Generally preferred is such use of 1,3-propanediol in an effective amount sufficient to accentuate or enhance a pleasant odor note(s) of the one odorant alcohol(s) and/or to mask or reduce an unpleasant odor note(s) of the one odorant alcohol(s).

By a sensory effective amount is meant a proportion of 1,3-propanediol sufficient to produce the above effects, i.e. highlighting or emphasizing a pleasant odor note and/or masking or an unpleasant odor note in the perfume mixture.

Advantageously, the effective amount of 1,3-propanediol is particularly suitable for accentuating or bringing out the natural freshness, vibrancy or floral odor note(s) of the one or more perfumes in the perfume mixture and/or for masking or reducing the greasy, technical or metallic odor notes of the one or more perfumes in the perfume mixture.

Surprisingly, the positive sensory properties of the one odorant alcohol or the plurality of odorant alcohols described above are accentuated and the negative sensory properties of the one odorant alcohol or the plurality of odorant alcohols described above are masked or repressed by combination with an effective amount of >10% by weight of 1,3-propanediol.

Preferably, the sensory properties of the one or more odorant alcohols described above are accentuated, masked or repressed when 1,3-propanediol is used in an amount of >10% by weight to 90% by weight. Even more preferably, the above-described sensory properties of the one or more odorant alcohols are modified when 1,3-propanediol is used in an amount of from 20 wt. % to 80 wt. %. Even more preferably, the sensory properties of the one odorant alcohol or the plurality of odorant alcohols described above are modified when 1,3-propanediol is used in an amount of from 30 wt % to 70 wt %. Even more preferably, the previously described sensory properties of the one odorant alcohol or the plurality of odorant alcohols are modified when 1,3-propanediol is used in an amount of from 40% to 60% by weight. Most preferably, the previously described sensory properties of the one odorant alcohol or the plurality of odorant alcohols are modified when 1,3-propanediol is used in an amount of >50% by weight. All amounts are based on the total weight of the perfume mixture.

Particularly advantageous effects, i.e. the highlighting or accentuation of pleasant odor notes of an odorant alcohol or the masking or reduction of unpleasant odor notes of an odorant alcohol, are achieved when in the use according to the invention according to the fourth aspect the quantity ratio of 1,3-propanediol to total quantity of odorant alcohol (s) is 40:60, preferably 20:80 and particularly preferably 10:90, or in particular the quantity ratio of 1,3-propanediol to total quantity of odorant alcohol(s) with green odor note is 40:60, preferably 20:80 and particularly preferably 10:90, or in particular the quantity ratio of 1,3-propanediol to total quantity of odorant alcohol(s) with floral odor note is 40:60, preferably 20:80 and particularly preferably 10:90.

Therefore, based on the beneficial effects previously described, the present invention according to a fifth aspect relates to the use of 1,3-propanediol for preparing a non-aqueous perfuming composition comprising or consisting of (i) >10% by weight of 1,3-propanediol; and (ii) one or more odorant(s) from the group of odorant alcohols, in particular from the group of odorant alcohols with green odor notes and/or from the group of odorant alcohols with floral odor notes.

Surprisingly, by using a sufficient or effective amount of 1,3-propanediol, a perfume mixture, preferably a perfume oil, can be prepared, whereby the sensory properties of an odorant alcohol or several odorant alcohols can be modified.

In particular, by using an effective amount of 1,3-propanediol, a perfume mixture can be prepared whereby a pleasant odor note or all of the pleasant odor notes of an odorant alcohol, can be emphasized or enhanced. For example, the perfume mixture may be modified to emphasize or enhance the radiance, natural freshness, or floral odor note(s) of the odorant alcohol or alcohols when 1,3-propanediol is used in an effective amount.

In an analogous manner, the use of an effective amount of 1,3-propanediol according to the invention can be used to prepare a perfume mixture, whereby in particular an unpleasant odor note or all unpleasant odor notes of an odorant alcohol, for example musty, greasy, technical or metallic odor note(s) of an odorant alcohol or several odorant alcohols, are masked or reduced.

The use of 1,3-propanediol thus allows the preparation of a perfume mixture comprising one or more odorant alcohol(s) in which the pleasant odor notes are enhanced and the unpleasant odor notes are reduced. Advantageously, the use of 1,3-propanediol allows the preparation of a perfume mixture comprising one or more odorant alcohol(s) which has more radiance or more natural freshness, or in which the floral odor notes are accentuated while greasy, technical or metallic odor notes are reduced.

The one, more or all of the odorant alcohol(s) whose odor properties are improved by the use of 1,3-propanediol according to the invention is preferably one or more odorant alcohol(s) with a green odor note or one or more odorant alcohol(s) with a floral odor note.

Generally preferred is/are the one, more or all of the unpleasant and/or pleasant smelling, green smelling odorant alcohol(s) selected from the group consisting of odorant alcohols having a molecular weight in the range of from 100 g/mol to 190 g/mol, preferably in the range of from 100 g/mol to 158 g/mol.

In a preferred embodiment, the one or more green-smelling odorant alcohols are selected from the group consisting of C6 alcohol, C7 alcohol, (Z)-3-hexenol (cis-3-hexenol), (E)-2-hexenol (trans-2-hexenol), (E/Z)-3-hexenol, and (Z)-4-hexenol (cis-4-hexenol).

Alternatively preferred is/are the one, more or all of the unpleasant and/or pleasant-smelling odorant alcohol(s) having a floral odor selected from the group consisting of odorant alcohols having a molecular weight in the range of from 120 g/mol to 200 g/mol, preferably in the range of from 122 to 168 g/mol.

In a preferred embodiment, the one or more odorant alcohols having a floral odor are selected from the group consisting of phenylethyl alcohol, linalool, citronellol, geraniol, nerol, ethyllinalool, tetrahydrolinalool, dihydromyrcenol, C8 alcohol, C9 alcohol, C10 alcohol, alpha-terpineol and tetrahydromyrcenol.

Even more preferred are either two, three, four, five or more different odorant alcohols selected from the group of odorant alcohols with green odor note consisting of C6-alcohol, C7-alcohol, (Z)-3-hexenol (cis-3-hexenol), (E)-2-hexenol (trans-2-hexenol), (E/Z)-3-hexenol and (Z)-4-hexenol (cis-4-hexenol), and/or from the group of odorant alcohols with a floral odor, which consists of phenylethyl alcohol, linalool, citronellol, geraniol, nerol, ethyllinalool, tetrahydrolinalool, dihydromyrcenol, C8 alcohol, C9 alcohol, C10 alcohol, alpha-terpineol and tetrahydromyrcenol.

Surprisingly, the sensory properties of the one or more odorant alcohols are positively influenced by combination with an effective amount of 1,3-propanediol. In individual cases, the sensory impression is shifted in the direction of more natural, fresher, more radiance, less musty, less artificial and less metallic, whereby in individual cases further sensory influences were also observed in the presence of 1,3-propanediol.

Even more preferred are comprising two, three, four, five or more different odorant alcohols from the group of odorant alcohols having green odor notes and/or comprising two, three, four, five or more different odorant alcohols from the group of odorant alcohols having floral odor notes.

With regard to the ingredients (i) and (ii), their preferred or alternative embodiments and their mixing and quantity ratios, as well as their beneficial effects, reference is made to the above detailed description in connection with the perfume mixture according to the invention, which is equally valid for the use according to the invention in accordance with the fifth aspect of the invention, so that it is unnecessary to repeat it.

The 1,3-propanediol is used in the use according to the invention for the preparation of a non-aqueous perfume mixture in an amount of >10% by weight. Preferably, 1,3-propanediol is used in the use according to the invention in an amount of >10 wt % to 90 wt %. Even more preferably, 1,3-propanediol is used in the use according to the invention in an amount of from 20 wt % to 80 wt %. Still more preferably, 1,3-propanediol is used in the use according to the invention in an amount of from 30 wt % to 70 wt %. Still more preferably, in the use according to the invention, 1,3-propanediol is used in an amount of 40 wt %. to 60 wt %. Most preferably, in the use according to the invention, 1,3-propanediol is used in an amount of >50 wt %. All quantities are based on the total weight of the perfume mixture.

Particularly advantageous effects, i.e. the highlighting or accentuation of pleasant odor notes of an odorant alcohol or the masking or particularly advantageous effects, i.e. the highlighting or accentuation of pleasant odor notes of an odorant alcohol or the masking or reduction of unpleasant odor notes of an odorant alcohol, are achieved when, in the use of 1,3-propanediol for the preparation of a perfume mixture according to the fifth aspect, the quantitative ratio of 1,3-propanediol to total amount of odorant alcohol(s) is 50:50, preferably 40:60, even more preferably 20: 80 and most preferably 10:90, or in particular the quantitative ratio of 1,3-propanediol to total amount of odorant alcohol(s)

with green odor note is 50:50, preferably 40:60, even more preferably 20:80 and most preferably 10:90, or in particular the quantitative ratio of 1,3-propanediol to total amount of odorant alcohol(s) with floral odor note is 50:50, preferably 40:60, even more preferably 20:80 and most preferably 10:90.

Another aspect of the invention relates to the use of the odorant mixture or perfume mixture according to the invention in a sensory effective amount for imparting, modifying or enhancing the sensory properties or an odor note of a perfumed product or for preparing a perfumed product.

Due to its advantageous primary, i.e. olfactory, and secondary properties as described above, the perfuming composition according to the invention is eminently suitable for perfuming or fragrancing, i.e. for imparting, modifying or enhancing the sensory properties of a perfumed product or for preparing a perfumed product.

To effectively impart, modify or enhance sensory properties, the perfume mixture must be used in a sensory effective amount.

Perfuming is understood to mean the imparting of a sensory olfactory impression, i.e. an olfactory effect or an additional olfactory effect. Perfuming of a product in the strict sense is to be distinguished from a reduction of an unpleasant odor (as described above) and may occur in addition to such a reduction.

The term “sensory effective amount” means, in the context of the present application, that the perfume mixture or perfume mixture is used in such a sufficient amount that the resulting product, in use or in use, reveals the sensory properties of the perfume mixture according to the invention.

As regards the perfume mixture, its preferred or alternative embodiments, its components (i) and (ii), their mixing and quantitative ratios, and its beneficial effects, reference is made to the above detailed description in connection with the perfume mixture according to the invention according to the first aspect, which is equally valid for the use of the perfume mixture according to the invention for imparting, modifying or enhancing the sensory properties of a perfumed product or for preparing a perfumed product, so that it is unnecessary to repeat it.

According to a further aspect, the present invention relates to a perfumed product comprising the inventive perfume mixture or perfume mixture, preferably the perfume oil, in a sensory effective amount.

The perfumed products, such as cosmetic compositions, application compositions or washing and cleaning compositions, or their further ingredients or composition, are preferably those as described in detail in paragraphs [0074] to [0204] of WO 2018/114073 A1. This disclosure is incorporated by specific reference in its entirety in the present application.

In the manufacture of the perfumed products, the perfume mixtures or perfume mixtures according to the invention are used in liquid form, undiluted or diluted with a solvent, for perfuming purposes. Suitable solvents include ethanol, isopropyl alcohol, diethylene glycol monoethyl ether, glycerol, propylene glycol, 1,2-butylene glycol, dipropylene glycol, diethyl phthalate, triethyl citrate, isopropyl myristate, etc.

These perfume mixtures may contain up to 90% by weight, preferably from about 5% to about 70% by weight, more preferably from about 10% to about 50% by weight, and particularly preferably from about 15% to about 25% by weight of said solvents.

In the preparation of the perfumed products, the perfume mixtures according to the invention are preferably combined with further ingredients. Preferred further ingredients are selected from the group consisting of:

Preservatives, preferably those mentioned in US 2006/0089413, abrasives, anti-acne agents and sebum reducing agents, preferably those mentioned in WO 2008/046791, anti-aging agents, preferably those mentioned in WO 2005/123101, antibacterial agents, anticellulite agents, anti-dandruff agents, preferably those mentioned in WO 2008/046795, anti-inflammatory agents, anti-irritants (anti-inflammatory, anti-irritant and anti-irritant agents), preferably those mentioned in WO 2007/042472 and US 2006/0089413, antimicrobial agents, preferably those mentioned in WO 2005/123101, antioxidants, preferably those mentioned in WO 2005/123101, astringents, antiseptic agents, antistatic agents, binders, buffers, carriers, preferably those mentioned in WO 2005/123101, chelating agents, preferably those mentioned in WO 2005/123101, cell stimulants, cleansing agents, conditioning agents, depilatories, surfactants, deodorants and antiperspirants, preferably those mentioned in WO 2005/123101, emollients, emulsifiers, preferably those mentioned in WO 2005/123101, enzymes, essential oils, preferably those mentioned in US 2008/0070825, insect repellents, preferably those mentioned in WO 2005/123101, fibers, film formers, fixatives, foaming agents, foam stabilizers, anti-foaming substances, foam boosters, fungicides, gelling agents and gelling agents, preferably those mentioned in WO 2005/123101, hair care agents, hair shaping agents, hair smoothing agents, moisture regulators (moisturizing, moistening and/or moisture retaining substances), preferably those mentioned in WO 2005/123101, osmolytes, preferably those mentioned in WO 2005/123101, compatible solutes, preferably those mentioned in WO 01/76572 and WO 02/15686, bleaching agents, strengthening agents, stain removing agents, optically brightening agents, impregnating agents, soil-repellent agents, friction-reducing agents, lubricants, moisturizers, ointments, opacifiers, plasticizing agents, covering agents, polishes, brighteners, polymers, preferably those mentioned in WO 2008/046676, powders, proteins and protein hydrolysates, preferably those mentioned in WO 2005/123101 and WO 2008/046676, refatting agents, abrasive agents, skin-soothing agents, skin-cleansing agents, skin-caring agents, skin repair agents, preferably containing cholesterol and/or fatty acids and/or ceramides and/or pseudoceramides, preferably those mentioned in WO 2006/053912, skin lightening agents, preferably those mentioned in WO 2007/110415, skin protecting agents, skin softening agents, skin cooling agents, preferably those mentioned in WO 2005/123101, skin warming agents, preferably those mentioned in WO 2005/123101, stabilizers, UV absorbing agents and UV filters, preferably the benzylidene beta-dicarbonyl compounds mentioned in WO 2005/123101, preferably the alpha-benzoyl cinnamic acid nitriles mentioned in WO 2005/107692, preferably the AhR receptor antagonists mentioned in WO 2006/015954, preferably those mentioned in WO 2007/128723 and WO 2007/060256, detergents, fabric softeners, suspending agents, skin tanning agents, preferably those mentioned in WO 2006/045760,—thickening agents, vitamins, preferably those mentioned in WO 2005/123101, oils, waxes and fats, preferably those mentioned in WO 2005/123101, phospholipids, preferably those mentioned in WO 2005/123101, fatty acids (saturated fatty acids, mono- or polyunsaturated fatty acids, a-hydroxy acids, polyhydroxy fatty acids), preferably those mentioned in WO 2005/123101, liquefiers, colorants and color-protecting agents as well as pigments, preferably those mentioned in WO 2005/123101, anticorrosives, flavors and aromas, preferably those mentioned in S. Arctander, Perfume and Flavor Chemicals, self-published, Montclair, N.J., 1969 and Surburg, Panten, Common Fragrance and Flavor Materials, 6th. Edition, Wiley-VCH, Weinheim, 2016 listed, in particular the further fragrances explicitly mentioned in US 2008/0070825, which are not already components of the perfume oil mixture according to the invention, alcohols and polyols, preferably the surfactants mentioned in WO 2005/123101, preferably those mentioned in WO 2005/123101, animal extracts, yeast extracts, extracts of algae or microalgae, electrolytes, liquefiers, organic solvents, preferably those mentioned in WO 2005/123101, or silicones and silicone derivatives, preferably those mentioned in WO 2008/046676.

For some applications, it is also advantageous to use the perfume mixtures of the invention adsorbed to a carrier which provides both a fine distribution of the fragrances in the product and a controlled release upon application. Such carriers may be porous inorganic materials such as light sulfate, silica gels, zeolites, gypsums, clays, clay granules, aerated concrete, etc., or organic materials such as woods, cellulose-based materials, sugars or plastics such as PVC, polyvinyl acetates or polyurethanes.

For other applications, it is advantageous to use the perfume mixture or perfume mixture of the invention microencapsulated, spray-dried, as an inclusion complex or as an extrusion product and to add it in this form to the (pre) product to be perfumed.

If necessary, the properties of the compositions modified in this way can be further optimized by so-called "coating" with suitable materials with a view to a more specific release of fragrance, for which purpose waxy plastics such as polyvinyl alcohol are preferably used. The resulting products are in turn products according to the invention.

As regards the aforementioned form of application of the perfume mixtures according to the invention, reference is made to the above description in connection with the perfume mixture according to the first aspect of the present invention, which is equally valid in the case of the preparation of the perfumed products, so that it is unnecessary to repeat it.

In a preferred embodiment of the present invention, the perfumed products perfumed or scented with the perfume mixture according to the invention are selected from the group consisting of: Perfume extracts, eau de parfums, eau de toilettes, shaving waters, eau de colognes, pre-shave products, splash colognes, perfumed-refreshing wipes, acidic, alkaline and neutral cleaning products such as floor cleaners, window glass cleaners, dishwashing detergents, bathroom and sanitary cleaners, —scouring powders, solid and liquid WC cleaners, powder and foam carpet cleaners, liquid laundry detergents, powder laundry detergents, laundry pre-treatment products, e.g. such as bleach, softeners and stain removers, fabric softeners, laundry soap, laundry tablets, disinfectants, surface disinfectants, air fresheners in liquid, gel or solid form, aerosol sprays, waxes and polishes such as furniture polishes, floor waxes, shoe polishes, personal care products such as solid and liquid soaps, shower gels, shampoos, shaving soaps, shaving foams, bath oils, cosmetic emulsions of the oil-in-water, water-in-oil and water-in-oil-in-water types, such as skin creams and lotions, facial creams and -lotions, sunscreen creams and lotions, aftersun creams and lotions, hand creams and lotions, —foot creams and lotions, depilatory creams and lotions, after-shave creams and lotions, tanning creams and lotions, hair care products such as e.g. hair sprays, hair gels, hair lotions, hair conditioners, permanent and semi-permanent hair dyes, hair shaping products such as cold waves and hair straighteners, hair tonics, hair creams and lotions, deodorants and antiperspirants such as underarm sprays, roll-ons, deodorant sticks, deodorant creams, decorative cosmetic products, candles, lamp oils, incense sticks, insecticides, repellents and propellants.

Particularly preferred perfumed products comprising the perfuming mixture according to the invention are selected from the group consisting of:

Eau de parfums, eau de toilettes, shaving waters (after-shave), eau de colognes, pre-shave products, splash colognes;

Acidic, alkaline and neutral cleaning agents, especially in the household sector, preferably floor cleaners, window glass cleaners, dishwashing detergents, bathroom and sanitary cleaners, scouring agents, solid and liquid WC cleaners, powder and foam carpet cleaners, liquid detergents, powder detergents, fabric softeners, surface disinfectants, especially for hard surfaces (hard surface cleaner);

Personal care products, preferably solid and liquid soaps, shower gels, shampoos, shaving soaps, shaving foams;

cosmetic emulsions of the oil-in-water, water-in-oil and water-in-oil-in-water types, preferably skin creams and lotions, face creams and lotions, sunscreen creams and lotions, after-sun creams and lotions, hand creams and lotions, foot creams and lotions, depilatory creams and lotions, after-shave creams and lotions, skin tanning creams and lotions, skin whitening creams and lotions;

Hair care products, preferably hair sprays, hair gels, setting hair lotions, hair conditioners, permanent and semi-permanent hair dyes, hair tonics, hair creams and lotions;

Deodorants and antiperspirants, preferably underarm sprays, roll-ons (preferably as alcoholic or non-alcoholic solution, as gel or (micro)emulsion, deosticks (deodorant sticks), deodorant creams.

Particularly preferred perfumed products according to the invention are washing and cleaning agents, hygiene or care products, in particular in the field of body and hair care, cosmetics and household.

In a preferred embodiment, the present invention relates to perfumed products containing the perfume mixture according to the invention comprising 1,3-propanediol and one or more perfume(s) from the group of odorant alcohols, preferably from the group of odorant alcohols with green notes and/or from the group of odorant alcohols with floral notes, in amounts of from about 0.01 to about 10 wt. %, preferably in amounts of about 0.1 to about 5% by weight and particularly preferably about 0.25 to about 3% by weight, in each case based on the total weight of the perfumed product.

The washing and cleaning compositions (abbreviated as WSR compositions) containing the perfume mixture according to the invention, within the meaning of the present invention, may be in solid form as powders, granules, tablets and the like, but also in liquid, gel or paste form. Preferably, these are detergents suitable for both manual or machine washing, in particular of textiles. They may also be washing or cleaning compositions for the industrial sector or for the household sector. Cleaning agents may also be used, for example, for cleaning hard surfaces. They may be, for example, dishwashing detergents used for manual or machine cleaning of dishes. They may also be common industrial or household cleaners used to clean hard surfaces such as furniture surfaces, tiles, tiles, wall and floor coverings. In addition to crockery, all other hard surfaces, in particular those made of glass, ceramics, plastic or metal, in the household and industry can also be considered as hard surfaces.

The WSR agents may have other commercially available ingredients, such as surfactants, builders, bleaching agents, bleach activators, thickeners, enzymes, electrolytes, pH adjusters, colorants and fragrances, foam inhibitors, antiredeposition agents, optical brighteners, graying inhibitors, wrinkle inhibitors, antimicrobial agents, preservatives, antioxidants, antistatic agents, UV adsorbers, heavy metal complexing agents, and the like.

Finally, the present invention also relates to a process for preparing a perfumed product comprising the following steps:

(a1) providing the perfume mixture according to the invention,
(b1) providing a further constituent or constituents of the perfumed product to be produced; and
(c1) contacting or mixing a sensory effective amount of the perfume mixture provided in step (a1) with the further ingredient(s) provided in step (b1) to obtain the perfumed product.

In this case, the amount of 1,3-propanediol (i) in the perfume mixture is >10% by weight in order to highlight or emphasize a pleasant odor note or all of the pleasant odor notes of the one or more odorant alcohols (ii) of the to emphasize or accentuate the one or more odorant alcohols (ii) of the odorant mixture, and/or mask or reduce an unpleasant odor note or all of the unpleasant odor notes of the one or more odorants (ii) of the mask or reduce the unpleasant odor note(s) of the one or more odorants (ii) of the odorant mixture.

In a preferred embodiment of the method, the amount of 1,3-propanediol (i), as defined above, in the perfume mixture is sufficient to highlight or accentuate the pleasant odor note(s) more radiance, natural freshness or floral odor note(s) of the one or more odorant alcohols (ii) of the perfume mixture; and/or the unpleasant odor note(s) musty, fatty, technical or metallic odor note(s) of the one or more odorant alcohols (ii) of the perfume mixture. mask or reduce any unpleasant odor note(s) of musty, fatty, technical or metallic odor note(s) of the one or more odorant alcohols (ii) of the odorant mixture.

An alternative variation of the process for preparing a perfumed product, comprises the following steps:

(a2) providing one or more odorant alcohols (ii) of the perfume mixture according to the invention,
(b2) providing a further component or components of the perfumed product to be manufactured,
(c2) mixing a sensory effective amount of the odorant alcohol(s) provided in step (a2) or the odorant alcohols (ii) with the further ingredient(s) provided in step (b2) to obtain a mixture, and a mixture, and
(d2) contacting the mixture obtained in step (c2) with 1,3-propanediol in an amount of >10% by weight.

In this respect, the amount of 1,3-propanediol (i) in the odorant mixture is sufficient to accentuate or enhance a pleasant odor note or all pleasant odor notes of the one odorant alcohol or the multiple odorant alcohols (ii) of the odorant mixture, and/or mask or reduce an unpleasant odor note or all unpleasant odor notes of the one or more odorant alcohols (ii) of the odorant mixture.

In a preferred embodiment of the method, the amount of 1,3-propanediol (i), as defined above, in the perfume mixture is sufficient to accentuate or enhance the pleasant odor note(s) more radiance, natural freshness or floral odor note(s) of the one or more odorant alcohols (ii) of the perfume mixture; and/or to accentuate or enhance the unpleasant odor note(s) musty, fatty, technical or metallic odor note(s) of the one or more odorant alcohols (ii) of the perfume mixture. mask or reduce any unpleasant odor note(s) of musty, fatty, technical or metallic odor note(s) of the one or more odorant alcohols (ii) of the odorant mixture.

The present invention will now be described and illustrated in more detail with reference to further examples, and the present invention is not limited to these examples.

EXAMPLES

Example 1

Sensory evaluation of 10% solutions of odorant alcohols in 1,3-propanediol in comparison with 10% solutions of odorant alcohols in dipropylene glycol (DPG)

For an explanation of the product names of fragrance materials, see, for example, S. Arctander, Perfume and Flavor Materials, Volumes I and II, Montclair, N. J., 1969, self-published, or H. Surburg, J. Panten, "Common Fragrance and Flavor Materials," 6th edition, Wiley-VCH, Weinheim, 2016.

The sensory evaluation was carried out as follows: The evaluation of the odor was carried out by eight sensory trained test persons. For this purpose, the above test solutions were filled into closed glasses. The samples were coded, tested in randomized order and under exclusion of disturbing influences such as color, noise and foreign odors in a sensory room. Two olfactory strips were each immersed in two test solutions and scored in pairs. Each subject noted their olfactory perception. The final score for a sample was then determined by matching/parallel terms.

TABLE 3

| No. | Odorant alcohol Group | Name Molecular weight (MG) | Structure | Smell (compared to the 10% DPG solution) |
|---|---|---|---|---|
| 1 | Flowery | Phenylethyl alcohol MG: 122.16 g/mol | 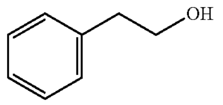 | more volume, more radiation, juicier, fruitier, fresh |
| 2 | Flowery | Linalool MG: 154.25 g/mol | 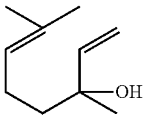 | juicy-fruit, less sweet |

TABLE 3-continued

| No. | Odorant alcohol Group | Name Molecular weight (MG) | Structure | Smell (compared to the 10% DPG solution) |
|---|---|---|---|---|
| 3 | Flowery | Citronellol MG: 156.27 g/mol | 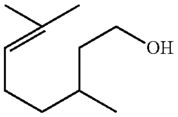 | more volume, more radiation, tangy |
| 4 | Flowery | Geraniol MG: 154.25 g/mol | 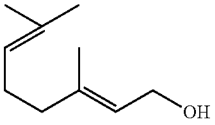 | reduces the sulphur note, makes it fruitier, fruit pulp character, natural |
| 5 | Flowery | Nerol MG: 154.25 g/mol | 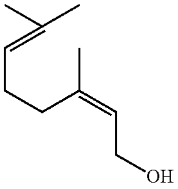 | changes the green note, takes away the grass-green peak, becomes more fruity and juicy, direction rhubarb |
| 6 | Flowery | Ethyllinalool MG: 168.28 g/mol | 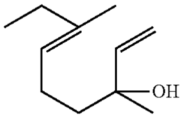 | reduces the sulphur note, becomes fruitier and tangier |
| 7 | Flowery | Tetrahydrolinalool MG: 158.285 g/mol | 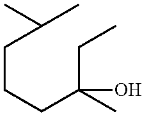 | more volume, sweet and sour |
| 8 | Flowery | Dihydromyrcenol MG: 156.27 g/mol | 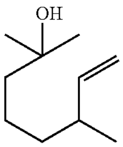 | more volume, fruit note changes from grapefruit towards ripe banana |
| 9 | Green | Alcohol C6 MG: 102.162 g/mol | 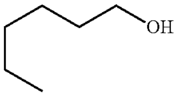 | fresh and tangy, citric note, more banana unripe |
| 10 | Green | Alcohol C7 MG: 116.88 g/mol | 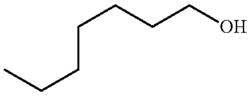 | strawberry, a little aniseed, fresher, natural |
| 11 | Flowery | Alcohol C8 MG: 130.23 g/mol | 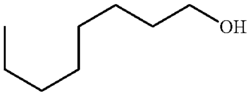 | less green, fruity, rounder, covers the technically sharp note |
| 12 | Flowery | Alcohol C9 MG: 144.26 g/mol | 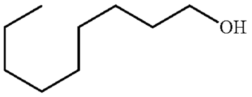 | fruity, sweet, more ripe fruit |
| 13 | Flowery | Alcohol C10 MG: 158.28 g/mol | 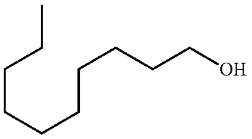 | covers sulphur note, less aggressive, mild |

TABLE 3-continued

| No. | Odorant alcohol Group | Name Molecular weight (MG) | Structure | Smell (compared to the 10% DPG solution) |
|---|---|---|---|---|
| 14 | Flowery | Terpineol alpha MG: 154.15 g/mol | 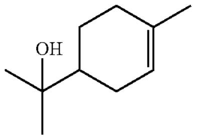 | more volume, fresh unripe fruit note |
| 15 | Green | (Z)-3-hexenol MG: 100.16 g/mol | 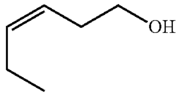 | more volume, more watery, more transparent, fresh |
| 16 | Green | (E)-2-hexenol MG: 100.16 g/mol | 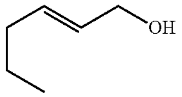 | more volume, juicy-fruity |
| 17 | Green | (E/Z)-3-hexenol MG: 100.16 | 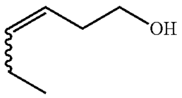 | more volume, more radiation, sharper, more sting, fresh |
| 18 | Flowery | Tetrahydromyrcenol MG: 158.28 g/mol | 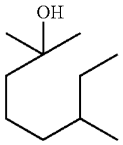 | more flowery, overlays green flower cutting note |
| 19 | Green | (Z)-4-hexenol MG: 100.16 g/mol | | more volume, more radiation less metallic, fresher, rounder, not so greasy |

The 10% solutions of the odorant alcohols in 1,3-propanediol were perceived stronger and with less unpleasant side notes than the 10% solutions of the odorant alcohols in DPG. The solutions in 1,3-propanediol appear more floral and natural and have more volume.

Example 2

Sensory evaluation of 10-%, 20-%, 40-% and 60-% solutions of the odorant alcohols in 1,3-propanediol For an explanation of the product names of fragrance materials, see, for example, S. Arctander, Perfume and Flavor Materials, Volumes I and II, Montclair, N. J., 1969, self-published, or H. Surburg, J. Panten, "Common Fragrance and Flavor Materials," 6th edition, Wiley-VCH, Weinheim, 2016.

The sensory evaluation was carried out as follows: The evaluation of the odor was carried out by eight sensory trained test persons. For this purpose, the above test solutions were filled into closed glasses. The samples were coded, tested in randomized order and under exclusion of disturbing influences such as color, noise and foreign odors in a sensory room. Two olfactory strips were each immersed in two test solutions and scored in pairs. Each subject noted their olfactory perception. The final score for a sample was then determined by matching/parallel terms.

TABLE 4

| | | | Smell | | | | |
|---|---|---|---|---|---|---|---|
| No: | Name | Structure | pure | 10% | 20% | 40% | 60% |
| 1 | Phenylethyl alcohol | 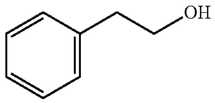 (122) | Rosy honey-like, green, greasy | more impact, more radiation, juicy-fruity, fresher | less greasy, fresher, sweeter | more natural greener, more radiation | more floral, juicy, fresh |

TABLE 4-continued

| No: | Name | Structure | Smell pure | 10% | 20% | 40% | 60% |
|---|---|---|---|---|---|---|---|
| 2 | Linalool | 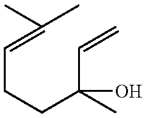 (154) | Floral bright fresh light citrus note with woody notes | juicier, fruitier, | Clearer, brighter | Slightly floral, fresh | flowerier, cleaner |
| 3 | Citronellol | 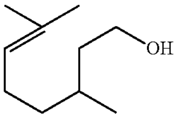 (156) | Fresh, rosy, floral, bright, fresh | more impact, more radiation, splashier | fresher, more radiation, | more rose, more impact | more citrusy, softer, |
| 4 | Geraniol | 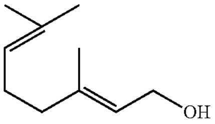 (154) | Sweet, floral-rosy, light fruity | reduces the sulphur note, makes fruity, fruit character, natural | light fruity, more natural | Harmonious, flowery, natural | Softer, less greasy, more natural |
| 1 | Phenylethyl alcohol | 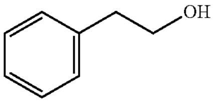 (122) | Rosy honey-like, green, greasy | more impact, more radiation, juicy-fruity, fresher | less greasy, fresher, sweeter | more natural greener, more radiation | more floral, juicy, fresh |
| 5 | Nerol | 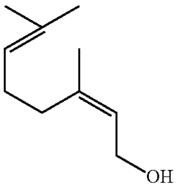 (154) | Fresh, rosy, floral, sweet, greenish | changes the green note, takes away the green-green peak, becomes more fruity-juicy towards rhubarb | more impact, more radiation, juicy-fruity, fresher | less greasy, fresher, sweeter, more impact | more natural floral, more raditation |
| 6 | Ethyllinallol | 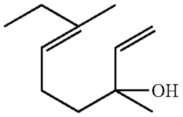 (168) | Floral woody-green, a little fruity | reduces the sulphur note, becomes more fruity and tangy | more impact, juicy-fruity, fresher | less greasy, fresher, sweeter | more natural floral, more freshness |
| 7 | Tetra-hydrolinalool | 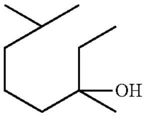 (158) | Fresh, citrus-floral, sweet, greenish | more impact, sweet-juicy | Not so greasy, stronger citrus notes | less greasy, fresher, sweeter | naturally greener, more radiation into the flowery |
| 1 | Phenylethyl alcohol | 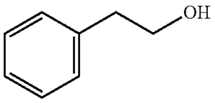 (122) | Rosy honey-like, green, greasy | more impact, more radiation, juicy-fruity, fresher | less greasy, fresher, sweeter | more natural greener, more radiation | more floral, juicy, fresh |

TABLE 4-continued

| No: | Name | Structure | Smell pure | 10% | 20% | 40% | 60% |
|---|---|---|---|---|---|---|---|
| 8 | Dihydro-myrcenol | 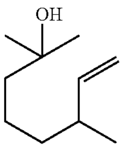 (156) | Fresh, citrus-floral sweet with woody undertone | more impact, fruit note changes from grapefruit to ripe banana | more radiation, juicy-fruity, fresh | Less woody, fresher, sweeter | Natural floral greener, more impact |

Depending on the concentration of 1,3-propanediol, the solutions of the olfactory alcohols disclosed above are perceived more strongly and with less unpleasant secondary notes. By varying the 1,3-propanediol concentration in the perfume mixture according to the invention, for example by increasing or decreasing the 1,3-propanediol content, the sensory properties of the perfume mixture and thus the sensory profile of the perfume mixture can be adjusted or varied.

Example 3

Composition of Perfume Oil Mixtures

TABLE 5

| Chord Rose | |
|---|---|
| Components | g |
| ALCOHOL C 7 | 1.5 |
| LINALOOL | 25 |
| GERANIUM OIL AEGYPT. | 20 |
| ROSE OXIDE HIGH CIS | 1.5 |
| PHENYLETHYL ALCOHOL | 200 |
| CITRONELLOL 950 | 67 |
| GERANIOL SUPRA | 400 |
| NEROL 900 | 195 |
| STRAIGHT GERANYL ACETATE | 45 |
| IONON ALPHA | 35 |
| EUGENOL NAT. | 10 |

TABLE 6

| Chord Freesia | |
|---|---|
| Component | g |
| ALCOHOL C 8 | 2 |
| ALCOHOL C10 | 3 |
| HEXENOL CIS-3 | 7.5 |
| HEXENOL TRANS-2 | 2.5 |
| DIHYDROMYRCENOL | 150 |
| FLOROSA | 95 |
| ETHYLLINALOOL | 65 |
| LINALOOL | 205 |
| TERPINEOL ALPHA | 95 |
| PHENYLETHYL ALCOHOL | 120 |
| CITRONELLOL 950 | 45 |
| GERANIOL 60 | 67 |
| PHENOXANOL | 55 |
| HELIOTROPIN/PIPERONAL | 35 |

Example 4

Sensory evaluation of solutions of the perfume oil mixtures according to example 3 in 1,3-propanediol and in DPG in comparison

TABLE 7

| Composition of the solutions | | | | |
|---|---|---|---|---|
| | Chord Rose | Chord Freesia | DPG | 1,3-Propanediol |
| Solution A | 80% | | 20% | |
| Solution B | 80% | | | 20% |
| Solution C | | 80% | 20% | |
| Solution D | | 80% | | 20% |
| Solution E | 50% | | 50% | |
| Solution F | 50% | | | 50% |
| Solution G | | 50% | 50% | |
| Solution H | | 50% | | 50% |

The sensory evaluation was carried out as follows: The evaluation of the odor was carried out by eight sensory trained test persons. For this purpose, the above solutions were filled into closed glasses. The samples were coded, tested in randomized order and under exclusion of disturbing influences such as color, noise and foreign odors in a sensory room. Two olfactory strips were each immersed in two test solutions and scored in pairs. Each subject noted their olfactory perception. The final score for a sample was then determined by matching/parallel terms.

Compared to solution A, solution B smells much more cosmetic, rosy, sweet and has more impact.

Compared to solution C, solution D smells much stronger, greener and more watery.

Compared to Solution, Solution F smells zippier, greener, rounder and has more volume.

Compared to solution G, solution H smells stronger, tangier, more flowery and fresher.

The invention claimed is:

1. A non-aqueous perfume mixture comprising (i) >10% by weight of 1,3-propanediol; and (ii) one or more odorant(s) from the group of odorant alcohols, selected from the group of odorant alcohols with green notes and/or the group of odorant alcohols with floral notes, wherein the one or more odorant alcohols having green notes is/are selected from the group consisting of C6 alcohol, C7 alcohol, (Z)-3-hexenol (cis-3-hexenol), (E)-2-hexenol (trans-2-hexenol), (E/Z)-3-hexenol and (Z)-4-hexenol (cis-4-hexenol), and/or wherein the one odorant alcohol and/or the plurality of one or more odorant alcohols having floral notes is/are selected from the group consisting of phenylethyl alcohol, linalool, citronellol, geraniol, nerol, ethyllinalool, tetrahydrolinalool, dihydromyrcenol, C8 alcohol, C9 alcohol, C10 alcohol, alpha-terpineol and tetrahydromyrcenol, wherein the amount of 1,3-propanediol in the perfume mixture is sufficient to:

to bring out or accentuate a pleasant odor note or all the pleasant odor notes of the one odorant alcohol or of the several odorant alcohols, and/or to mask or reduce an unpleasant odor note or all unpleasant odor notes of the one odorant alcohol or the plurality of odorant alcohols, and wherein the quantitative ratio of 1,3-propanediol to total amount of odorant alcohol(s) is in a range of 50:50 to 10:90, based on the total weight of the perfume mixture.

2. A perfume mixture according to claim 1, wherein the perfume mixture comprises one or more further fragrance(s) selected from the group of:

(1) Hydrocarbons;
(2) Aliphatic alcohols
(3) Aliphatic aldehydes and their acetals
(4) Aliphatic ketones and their oximes
(5) Aliphatic sulphur-containing compounds
(6) Aliphatic nitriles
(7) Esters of aliphatic carboxylic acids
(8) Acyclic terpene alcohols
(9) Acyclic terpene aldehydes and ketones;
(10) Cyclic terpene alcohols;
(11) Cyclic terpene aldehydes and ketones
(12) Cyclic alcohols;
(13) Cycloaliphatic alcohols;
(14) Cyclic and cycloaliphatic ethers;
(15) Cyclic and macrocyclic ketones;
(16) Cycloaliphatic aldehydes;
(17) Cycloaliphatic ketones;
(18) Esters of cyclic alcohols;
(19) Esters of cycloaliphatic alcohols;
(20) Esters of cycloaliphatic carboxylic acids;
(21) Araliphatic alcohols;
(22) Esters of araliphatic alcohols and aliphatic carboxylic acids;
(23) Araliphatic ethers;
(24) Aromatic and araliphatic aldehydes;
(25) Aromatic and araliphatic ketones;
(26) Aromatic and araliphatic carboxylic acids and their esters;
(27) Aromatic compounds containing nitrogen;
(28) Phenols, phenyl ethers and phenyl esters;
(29) Heterocyclic compounds;
(30) Lactones;

and mixtures of the above-mentioned fragrances.

3. The perfume mixture according to claim 1, wherein the amount of 1,3-propanediol in the non-aqueous perfume mixture is in a range of 20% to 80% by weight.

4. The perfume mixture according to claim 3, wherein the amount of 1,3-propanediol in the non-aqueous perfume mixture is in a range of 40% to 60% by weight.

5. A perfumed product comprising a sensory effective amount of the perfume mixture of claim 1.

6. The perfumed product of claim 5, wherein the product is selected from the group of:

perfume extracts, eau de parfums, eau de toilettes, shaving waters, eau de colognes, pre-shave products, splash colognes, perfumed refreshing wipes, acidic, alkaline and neutral cleaning products, floor cleaners, window glass cleaners, dishwashing detergents, bathroom and sanitary cleaners, scouring powders, solid and liquid WC cleaners, powder and foam carpet cleaners, liquid laundry detergents, powder laundry detergents, laundry pre-treatment products, bleach, softeners and stain removers, fabric softeners, laundry soap, laundry tablets, disinfectants, surface disinfectants, air fresheners in liquid, gel or solid form, aerosol sprays, waxes and polishes such as furniture polishes, floor waxes, shoe polishes, personal care products such as solid and liquid soaps, shower gels, shampoos, shaving soaps, shaving foams, bath oils, cosmetic emulsions of the oil-in-water, water-in-oil and water-in-oil-in-water types, skin creams and lotions, facial creams andlotions, sun creams and lotions, after sun creams and lotions, hand creams and lotions,-foot creams and lotions, depilatory creams and lotions, aftershave creams and lotions, tanning creams and lotions, hair care products, hair sprays, hair gels, hair lotions, hair conditioners, permanent and semi-permanent hair dyes, hair shaping products, cold waves and hair straighteners, hair tonics, hair creams and lotions, deodorants and antiperspirants, underarm sprays, roll-ons, deodorant sticks, deodorant creams, decorative cosmetic products, candles, lamp oils, incense, insecticides, repellents and propellants.

7. A method of making a perfumed product, comprising:

(a1) providing the perfume mixture according to claim 1, (b1) providing one or more further constituents of the perfumed product to be produced; and (c1) contacting or mixing a sensory effective amount of the perfume mixture provided in step (a1) with the further ingredient(s) provided in step (b1) to obtain the perfumed product;

wherein the amount of 1,3-propanediol (i) of the perfuming mixture is >10 wt. % in order to highlight or emphasize a pleasant odor note or all of the pleasant odor notes of the one or more odorant alcohols (ii) of the odorant mixture;

and/or mask or reduce an unpleasant odor note or all the unpleasant odor notes of the one or more odorant alcohols (ii) of the odorant mixture.

8. A process for preparing the non-aqueous perfume mixture of claim 1 comprising the steps of:

providing 1,3-propanediol;

providing one or more odorant alcohols selected from the group of odorant alcohols with green notes and/or the group of odorant alcohols with floral notes, wherein the one or more odorant alcohols having green notes is/are selected from the group consisting of C6 alcohol, C7 alcohol, (Z)-3-hexenol (cis-3-hexenol), (E)-2-hexenol (trans-2-hexenol), (E/Z)-3-hexenol and (Z)-4-hexenol (cis-4-hexenol), and/or wherein the one odorant alcohol and/or the plurality of one or more odorant alcohols having floral notes is/are selected from the group consisting of phenylethyl alcohol, linalool, citronellol, geraniol, nerol, ethyllinalool, tetrahydrolinalool, dihydromyrcenol, C8 alcohol, C9 alcohol, C10 alcohol, alpha-terpineol and tetrahydromyrcenol;

contacting and mixing an effective amount of >10% by weight of 1,3-propanediol with the one or more odorant alcohol or alcohols to obtain the non-aqueous perfuming mixture having the quantitative ratio of 1,3-propanediol to total amount of odorant alcohol(s) is in a range of 50:50 to 10:90, based on the total weight of the perfume mixture.

9. The method of claim 8, wherein the amount of 1,3-propanediol in the non-aqueous perfume mixture is in a range of 20% to 80% by weight.

* * * * *